United States Patent
Xie et al.

(10) Patent No.: US 11,504,414 B2
(45) Date of Patent: Nov. 22, 2022

(54) BACTERIAL INHIBITORS

(71) Applicant: Meharry Medical College, Nashville, TN (US)

(72) Inventors: Hua Xie, Nashville, TN (US); Richard J. Lamont, Louisville, KY (US)

(*) Notice: Subject to any disclaimer, the term of this patent is extended or adjusted under 35 U.S.C. 154(b) by 0 days.

(21) Appl. No.: 16/363,908

(22) Filed: Mar. 25, 2019

(65) Prior Publication Data

US 2019/0209646 A1 Jul. 11, 2019

Related U.S. Application Data

(63) Continuation of application No. PCT/US2017/051352, filed on Sep. 13, 2017.

(60) Provisional application No. 62/404,690, filed on Oct. 5, 2016, provisional application No. 62/401,572, filed on Sep. 29, 2016.

(51) Int. Cl.
| | |
|---|---|
| *A61K 38/16* | (2006.01) |
| *C12N 9/78* | (2006.01) |
| *C07K 14/315* | (2006.01) |
| *A61P 31/04* | (2006.01) |
| *A61K 9/00* | (2006.01) |
| *C12N 15/52* | (2006.01) |
| *A61K 38/00* | (2006.01) |

(52) U.S. Cl.
CPC .......... *A61K 38/164* (2013.01); *A61K 9/0053* (2013.01); *A61P 31/04* (2018.01); *C07K 14/315* (2013.01); *C12N 9/78* (2013.01); *C12N 15/52* (2013.01); *A61K 38/00* (2013.01); *C12Y 305/03006* (2013.01); *C12Y 305/03015* (2013.01)

(58) Field of Classification Search
None
See application file for complete search history.

(56) References Cited

U.S. PATENT DOCUMENTS

| | | |
|---|---|---|
| 2004/0005276 A1 | 1/2004 | Reynolds et al. |
| 2015/0366792 A1* | 12/2015 | Fagerberg .............. A61K 8/99 424/50 |

FOREIGN PATENT DOCUMENTS

EP 2256205 12/2010

OTHER PUBLICATIONS

Bowie et al (Science, 1990, 257:1306-1310).*
Burgess et al (J.of Cell Bio. 111:2129-2138, 1990).*
Lazar et al. (Molecularand Cellular Biology, 1988, 8:1247-1252).*
Bork (Genome Research, 2000,10:398-400).*
The International Search Report and the Written Opinion of the International Searching Authority of PCT/US2017/051352, dated Dec. 21, 2017.
Xie, H. et al., Streptococcus cristatus ArcA Interferes with Porphyromonas gingivalis Pathogenicity in Mice, Journal of Periodontal Research, 2012, p. 578-583, vol. 47, No. 5.
Xie, H. et al., Identification of a signalling molecule involved in bacterial intergeneric communications, Microbiology, 2007, p. 3228-3234, vol. 153.
Christopher, A. et al., A streptococcal effector protein that inhibits Porphyomonas gingivalis biofilm development, Microbiology, 2010, p. 3469-3477, vol. 156.
Olsen, I. et al., Strategies for the inhibition of gingipains for the potential treatment of periodontitis and associated systemic diseases, Jounral of Oral Microbiology, 2014, vol. 6.
Zheng, C. et al., Differential expression and adherence of Porphyromonas gingivalis FimA genotypes, Molecular Oral Microbiology, 2011, p. 388-395, vol. 26, No. 6.
Capestany, C. et al., Role of the Porphyromonas gingivalis InlJ protein in homotypic and heterotypic biofilm development, Infection and Immunity, 2006, p. 3002-3005, vol. 74.
Chaudhuri, S. et al., Identification of a diguanylate cyclase and its role in Porphyromonas gingivalis virulence, Infection and Immunity, 2014, p. 2728-2735, vol. 82, No. 7.
Kadowaki, T. et al., Arg-gingipain acts as a major processing enzyme for various cell surface proteins in Porphyromonas gingivalis, The Journal of Biological Chemistry, 1998, p. 29072-29076, vol. 273, No. 44.

* cited by examiner

*Primary Examiner* — Robert A Zeman
(74) *Attorney, Agent, or Firm* — Bradley Arant Boult Cummings LLP; Timothy L. Capria; Alexandra C. Lynn

(57) ABSTRACT

Peptides related to certain portions of the arginine deiminase enzyme from the bacterium *Streptococcus cristatus* are provided that disrupt the formation and composition of biofilms containing the oral pathogen *Porphyromonas gingivalis*, and also modulate the virulence of *P. gingivalis*. Pharmaceutical compositions containing such peptides and method of using the same are disclosed.

20 Claims, 14 Drawing Sheets

Specification includes a Sequence Listing.

SEQUENCE LISTING

```
<160> NUMBER OF SEQ ID NOS: 32

<210> SEQ ID NO 1
<211> LENGTH: 409
<212> TYPE: PRT
<213> ORGANISM: Streptococcus cristatus

<400> SEQUENCE: 1

Met Ser Thr His Pro Ile His Val Phe Ser Glu Ile Gly Lys Leu Lys
1               5                   10                  15

Lys Val Met Leu His Arg Pro Gly Lys Glu Leu Glu Asn Leu Leu Pro
            20                  25                  30

Asp Tyr Leu Glu Arg Leu Leu Phe Asp Asp Ile Pro Phe Leu Glu Asp
        35                  40                  45

Ala Gln Lys Glu His Asp Ala Phe Ala Gln Ala Leu Arg Asp Glu Gly
    50                  55                  60

Ile Glu Val Leu Tyr Leu Glu Lys Leu Ala Ala Glu Ser Leu Ile Ser
65                  70                  75                  80

Pro Glu Ile Arg Glu Gln Phe Ile Glu Glu Tyr Leu Glu Glu Ala Asn
                85                  90                  95

Ile Arg Gly Arg Glu Thr Lys Lys Ala Ile Arg Glu Leu Leu His Gly
            100                 105                 110

Ile Lys Asp Asn Gln Glu Leu Val Glu Lys Thr Met Ala Gly Val Gln
        115                 120                 125

Lys Ala Glu Leu Pro Glu Ile Pro Asp Glu Ala Lys Gly Leu Thr Asp
    130                 135                 140

Leu Val Glu Ser Asp Tyr Pro Phe Ala Ile Asp Pro Met Pro Asn Leu
145                 150                 155                 160

Tyr Phe Thr Arg Asp Pro Phe Ala Thr Ile Gly Asn Ala Val Ser Leu
                165                 170                 175

Asn His Met Phe Ala Asp Thr Arg Asn Arg Glu Thr Leu Tyr Gly Lys
            180                 185                 190

Tyr Ile Phe Lys Tyr His Pro Glu Tyr Ala Gly Lys Val Glu Leu Val
        195                 200                 205

Tyr Asn Arg Glu Glu Asp Thr Arg Ile Glu Gly Asp Glu Leu Val
    210                 215                 220

Leu Ser Lys Asp Val Leu Ala Val Gly Ile Ser Gln Arg Thr Asp Ala
225                 230                 235                 240

Ala Ser Ile Glu Lys Leu Leu Val Asn Ile Phe Lys Lys Asn Val Gly
                245                 250                 255
```

```
Phe Lys Lys Val Leu Ala Phe Glu Phe Ala Asn Asn Arg Lys Phe Met
                260                 265                 270

His Leu Asp Thr Val Phe Thr Met Val Asp Tyr Asp Lys Phe Thr Ile
        275                 280                 285

His Pro Glu Ile Glu Gly Asp Leu Arg Val Tyr Ser Val Thr Tyr Glu
    290                 295                 300

Asn Glu Lys Leu Lys Ile Val Glu Glu Lys Gly Asp Leu Ala Glu Leu
305                 310                 315                 320

Leu Ala Gln Asn Leu Gly Val Glu Lys Val His Leu Ile Arg Cys Gly
                325                 330                 335

Gly Gly Asn Ile Val Ala Ala Gly Arg Glu Gln Trp Asn Asp Gly Ser
        340                 345                 350

Asn Thr Leu Thr Ile Ala Pro Gly Val Val Val Tyr Asp Arg Asn
    355                 360                 365

Thr Val Thr Asn Lys Ile Leu Glu Glu Tyr Gly Leu Arg Leu Ile Lys
370                 375                 380

Ile Arg Gly Ser Glu Leu Val Arg Gly Arg Gly Pro Arg Cys Met
385                 390                 395                 400

Ser Met Pro Phe Glu Arg Glu Val
                405

<210> SEQ ID NO 2
<211> LENGTH: 202
<212> TYPE: PRT
<213> ORGANISM: Streptococcus cristatus

<400> SEQUENCE: 2

Val Tyr Asn Arg Glu Glu Asp Thr Arg Ile Glu Gly Gly Asp Glu Leu
1               5                   10                  15

Val Leu Ser Lys Asp Val Leu Ala Val Gly Ile Ser Gln Arg Thr Asp
                20                  25                  30

Ala Ala Ser Ile Glu Lys Leu Leu Val Asn Ile Phe Lys Lys Asn Val
        35                  40                  45

Gly Phe Lys Lys Val Leu Ala Phe Glu Phe Ala Asn Asn Arg Lys Phe
    50                  55                  60

Met His Leu Asp Thr Val Phe Thr Met Val Asp Tyr Asp Lys Phe Thr
65                  70                  75                  80

Ile His Pro Glu Ile Glu Gly Asp Leu Arg Val Tyr Ser Val Thr Tyr
                85                  90                  95

Glu Asn Glu Lys Leu Lys Ile Val Glu Glu Lys Gly Asp Leu Ala Glu
                100                 105                 110

Leu Leu Ala Gln Asn Leu Gly Val Glu Lys Val His Leu Ile Arg Cys
        115                 120                 125

Gly Gly Gly Asn Ile Val Ala Ala Gly Arg Glu Gln Trp Asn Asp Gly
    130                 135                 140

Ser Asn Thr Leu Thr Ile Ala Pro Gly Val Val Val Tyr Asp Arg
145                 150                 155                 160

Asn Thr Val Thr Asn Lys Ile Leu Glu Glu Tyr Gly Leu Arg Leu Ile
                165                 170                 175

Lys Ile Arg Gly Ser Glu Leu Val Arg Gly Arg Gly Pro Arg Cys
                180                 185                 190

Met Ser Met Pro Phe Glu Arg Glu Val
    195                 200

<210> SEQ ID NO 3
```

-continued

<211> LENGTH: 8
<212> TYPE: PRT
<213> ORGANISM: Streptococcus cristatus

<400> SEQUENCE: 3

Ile Arg Gly Arg Glu Thr Lys Lys
1               5

<210> SEQ ID NO 4
<211> LENGTH: 11
<212> TYPE: PRT
<213> ORGANISM: Streptococcus cristatus

<400> SEQUENCE: 4

Asn His Met Phe Ala Asp Thr Arg Asn Arg Glu
1               5                   10

<210> SEQ ID NO 5
<211> LENGTH: 16
<212> TYPE: PRT
<213> ORGANISM: Streptococcus cristatus

<400> SEQUENCE: 5

Val Tyr Asn Arg Glu Glu Asp Thr Arg Ile Glu Gly Gly Asp Glu Leu
1               5                   10                  15

<210> SEQ ID NO 6
<211> LENGTH: 11
<212> TYPE: PRT
<213> ORGANISM: Streptococcus cristatus

<400> SEQUENCE: 6

Asn Ile Phe Lys Lys Asn Val Gly Phe Lys Lys
1               5                   10

<210> SEQ ID NO 7
<211> LENGTH: 16
<212> TYPE: PRT
<213> ORGANISM: Streptococcus cristatus

<400> SEQUENCE: 7

Glu Leu Val Arg Gly Arg Gly Gly Pro Arg Cys Met Ser Met Pro Phe
1               5                   10                  15

<210> SEQ ID NO 8
<211> LENGTH: 1230
<212> TYPE: DNA
<213> ORGANISM: Artificial Sequence
<220> FEATURE:
<223> OTHER INFORMATION: Most likely non-degenerat sequence

<400> SEQUENCE: 8
atgagcaccc atccgattca tgtgtttagc gaaattggca aactgaaaaa agtgatgctg      60
catcgcccgg gcaaagaact ggaaaacctg ctgccggatt atctggaacg cctgctgttt     120
gatgatattc gtttctgga agatgcgcag aaagaacatg atgcgtttgc gcaggcgctg      180
cgcgatgaag gcattgaagt gctgtatctg gaaaaactgg cggcggaaag cctgattagc     240
ccggaaattc gcaacagtt tattgaagaa tatctggaag aagcgaacat tcgcggccgc      300
gaaaccaaaa aagcgattcg cgaactgctg catggcatta agataaacca ggaactggtg     360
gaaaaaacca tggcgggcgt gcagaaagcg gaactgccgg aaattccgga tgaagcgaaa     420
ggcctgaccg atctggtgga aagcgattat ccgtttgcga ttgatccgat gccgaacctg     480

| | |
|---|---|
| tattttaccc gcgatccgtt tgcgaccatt ggcaacgcgg tgagcctgaa ccatatgttt | 540 |
| gcggataccc gcaaccgcga aaccctgtat ggcaaatata tttttaaata tcatccggaa | 600 |
| tatgcgggca aagtggaact ggtgtataac cgcgaagaag atacccgcat tgaaggcggc | 660 |
| gatgaactgg tgctgagcaa agatgtgctg cggtgggca ttagccagcg caccgatgcg | 720 |
| gcgagcattg aaaaactgct ggtgaacatt tttaaaaaaa cgtgggctt taaaaaagtg | 780 |
| ctggcgtttg aatttgcgaa caaccgcaaa tttatgcatc tggataccgt gtttaccatg | 840 |
| gtggattatg ataaatttac cattcatccg gaaattgaag gcgatctgcg cgtgtatagc | 900 |
| gtgacctatg aaaacgaaaa actgaaaatt gtggaagaaa aaggcgatct ggcggaactg | 960 |
| ctggcgcaga acctgggcgt ggaaaaagtg catctgattc gctgcggcgg cggcaacatt | 1020 |
| gtggcggcgg gccgcgaaca gtggaacgat ggcagcaaca ccctgaccat tgcgccgggc | 1080 |
| gtggtggtgg tgtatgatcg caacaccgtg accaacaaaa ttctggaaga atatggcctg | 1140 |
| cgcctgatta aaattcgcgg cagcgaactg gtgcgcggcc gcggcggccc cgctgcatg | 1200 |
| agcatgccgt tgaacgcga agaagtgtaa | 1230 |

<210> SEQ ID NO 9
<211> LENGTH: 606
<212> TYPE: DNA
<213> ORGANISM: artificial sequence
<220> FEATURE:
<223> OTHER INFORMATION: Most likely non-degenerate sequence

<400> SEQUENCE: 9

| | |
|---|---|
| gtgtataacc gcgaagaaga tacccgcatt gaaggcggcg atgaactggt gctgagcaaa | 60 |
| gatgtgctgg cggtgggcat tagccagcgc accgatgcgg cgagcattga aaaactgctg | 120 |
| gtgaacattt ttaaaaaaaa cgtgggcttt aaaaaagtgc tggcgtttga atttgcgaac | 180 |
| aaccgcaaat ttatgcatct ggataccgtg tttaccatgg tggattatga taaatttacc | 240 |
| attcatccgg aaattgaagg cgatctgcgc gtgtatagcg tgacctatga aaacgaaaaa | 300 |
| ctgaaaattg tggaagaaaa aggcgatctg gcggaactgc tggcgcagaa cctgggcgtg | 360 |
| gaaaaagtgc atctgattcg ctgcggcggc ggcaacattg tggcggcggg ccgcgaacag | 420 |
| tggaacgatg gcagcaacac cctgaccatt gcgccgggcg tggtggtggt gtatgatcgc | 480 |
| aacaccgtga ccaacaaaat tctggaagaa tatggcctgc gcctgattaa aattcgcggc | 540 |
| agcgaactgg tgcgcggccg cggcggcccg cgctgcatga gcatgccgtt gaacgcgaa | 600 |
| gaagtg | 606 |

<210> SEQ ID NO 10
<211> LENGTH: 24
<212> TYPE: DNA
<213> ORGANISM: Artificial sequence
<220> FEATURE:
<223> OTHER INFORMATION: Most likely non-degenerate sequence

<400> SEQUENCE: 10

| | |
|---|---|
| attcgcggcc gcgaaaccaa aaaa | 24 |

<210> SEQ ID NO 11
<211> LENGTH: 33
<212> TYPE: DNA
<213> ORGANISM: artificial sequence
<220> FEATURE:
<223> OTHER INFORMATION: Most likely non-degenerate sequence

<400> SEQUENCE: 11
aaccatatgt ttgcggatac ccgcaaccgc gaa                                    33

<210> SEQ ID NO 12
<211> LENGTH: 48
<212> TYPE: DNA
<213> ORGANISM: Artificial sequence
<220> FEATURE:
<223> OTHER INFORMATION: Most likely nondegenerate sequence

<400> SEQUENCE: 12
gtgtataacc gcgaagaaga tacccgcatt gaaggcggcg atgaactg                    48

<210> SEQ ID NO 13
<211> LENGTH: 33
<212> TYPE: DNA
<213> ORGANISM: artificial sequence
<220> FEATURE:
<223> OTHER INFORMATION: Most likely non-degenerate sequence

<400> SEQUENCE: 13
aacattttta aaaaaacgt gggctttaaa aaa                                     33

<210> SEQ ID NO 14
<211> LENGTH: 48
<212> TYPE: DNA
<213> ORGANISM: Artificial sequence
<220> FEATURE:
<223> OTHER INFORMATION: Most likely non-degenerate sequence

<400> SEQUENCE: 14
gaactggtgc gcggccgcgg cggcccgcgc tgcatgagca tgccgttt                    48

<210> SEQ ID NO 15
<211> LENGTH: 20
<212> TYPE: DNA
<213> ORGANISM: Artificial sequence
<220> FEATURE:
<223> OTHER INFORMATION: PCR primer

<400> SEQUENCE: 15
cggaacgaat aacccagaga                                                   20

<210> SEQ ID NO 16
<211> LENGTH: 20
<212> TYPE: DNA
<213> ORGANISM: Artificial sequence
<220> FEATURE:
<223> OTHER INFORMATION: PCR primer

<400> SEQUENCE: 16
ctgaccaacg agaacccact                                                   20

<210> SEQ ID NO 17
<211> LENGTH: 18
<212> TYPE: DNA
<213> ORGANISM: Artificial sequence
<220> FEATURE:
<223> OTHER INFORMATION: PCR primer

<400> SEQUENCE: 17
cagatgggtt gttgctca                                                     18

<210> SEQ ID NO 18
<211> LENGTH: 20
<212> TYPE: DNA

```
<213> ORGANISM: Artificial sequence
<220> FEATURE:
<223> OTHER INFORMATION: PCR primer

<400> SEQUENCE: 18
atggaaagtg ctgctggtag                                                  20

<210> SEQ ID NO 19
<211> LENGTH: 22
<212> TYPE: DNA
<213> ORGANISM: Artificial sequence
<220> FEATURE:
<223> OTHER INFORMATION: PCR primer

<400> SEQUENCE: 19
ctattgggaa ctgctgtgtt ac                                               22

<210> SEQ ID NO 20
<211> LENGTH: 21
<212> TYPE: DNA
<213> ORGANISM: Artificial sequence
<220> FEATURE:
<223> OTHER INFORMATION: PCR primer

<400> SEQUENCE: 20
tcctcgcccc aataagaatt c                                                21

<210> SEQ ID NO 21
<211> LENGTH: 20
<212> TYPE: DNA
<213> ORGANISM: Artificial sequence
<220> FEATURE:
<223> OTHER INFORMATION: PCR primer

<400> SEQUENCE: 21
caacagcaac cagctaccgt                                                  20

<210> SEQ ID NO 22
<211> LENGTH: 20
<212> TYPE: DNA
<213> ORGANISM: Artificial sequence
<220> FEATURE:
<223> OTHER INFORMATION: PCR primer

<400> SEQUENCE: 22
cgttcatctc atcctgcccg                                                  20

<210> SEQ ID NO 23
<211> LENGTH: 24
<212> TYPE: DNA
<213> ORGANISM: Artificial sequence
<220> FEATURE:
<223> OTHER INFORMATION: PCR primer

<400> SEQUENCE: 23
gacggttatt aagaccatca acac                                             24

<210> SEQ ID NO 24
<211> LENGTH: 19
<212> TYPE: DNA
<213> ORGANISM: Artificial sequence
<220> FEATURE:
<223> OTHER INFORMATION: PCR primer

<400> SEQUENCE: 24
tccacgctgc gagcggtat                                                   19
```

<210> SEQ ID NO 25
<211> LENGTH: 20
<212> TYPE: DNA
<213> ORGANISM: Artificial sequence
<220> FEATURE:
<223> OTHER INFORMATION: PCR primer

<400> SEQUENCE: 25
aattccacca cggtaagcac                                              20

<210> SEQ ID NO 26
<211> LENGTH: 20
<212> TYPE: DNA
<213> ORGANISM: Artificial sequence
<220> FEATURE:
<223> OTHER INFORMATION: PCR primer

<400> SEQUENCE: 26
gagccgaatt gtttgtcgat                                              20

<210> SEQ ID NO 27
<211> LENGTH: 20
<212> TYPE: DNA
<213> ORGANISM: Artificial sequence
<220> FEATURE:
<223> OTHER INFORMATION: PCR primer

<400> SEQUENCE: 27
taatgggaag agcgagcagt                                              20

<210> SEQ ID NO 28
<211> LENGTH: 20
<212> TYPE: DNA
<213> ORGANISM: Artificial sequence
<220> FEATURE:
<223> OTHER INFORMATION: PCR primer

<400> SEQUENCE: 28
acagggcatt tagcacaacc                                              20

<210> SEQ ID NO 29
<211> LENGTH: 20
<212> TYPE: DNA
<213> ORGANISM: Artificial sequence
<220> FEATURE:
<223> OTHER INFORMATION: PCR primer

<400> SEQUENCE: 29
tgggtttaaa gggtgcgtag                                              20

<210> SEQ ID NO 30
<211> LENGTH: 20
<212> TYPE: DNA
<213> ORGANISM: Artificial sequence
<220> FEATURE:
<223> OTHER INFORMATION: PCR primer

<400> SEQUENCE: 30
caatcggagt tcctcgtgat                                              20

<210> SEQ ID NO 31
<211> LENGTH: 20
<212> TYPE: DNA
<213> ORGANISM: Artificial sequence
<220> FEATURE:

```
<223> OTHER INFORMATION: PCR primer

<400> SEQUENCE: 31
tccaatgcca aacctttact                                          20

<210> SEQ ID NO 32
<211> LENGTH: 20
<212> TYPE: DNA
<213> ORGANISM: Artificial sequence
<220> FEATURE:
<223> OTHER INFORMATION: PCR primer

<400> SEQUENCE: 32
atacgagtat cttcttcacg                                          20
```

BACTERIAL INHIBITORS

CROSS-REFERENCE TO RELATED APPLICATIONS

This application is a continuation of and cites the priority of PCT/US2017/051352 filed 13 Sep. 2017, which is currently pending, and cites the priority of U.S. 62/401,572 filed 29 Sep. 2016 and U.S. 62/404,690 filed 5 Oct. 2016. The contents of PCT/US2017/051352, U.S. 62/401,572 and U.S. 62/404,690 are incorporated herein by reference in their entireties.

STATEMENT REGARDING FEDERALLY SPONSORED RESEARCH OR DEVELOPMENT

This invention was made with government support under grant numbers DE022428, DE14699, DE025332, DE12505, DE023193 awarded by NIDCR; and under grant number RR024975 awarded by NCRR (now mediated by NCATS as grant number TR00045). The government has certain rights in the invention.

In this context "government" refers to the government of the United Sates of America.

BACKGROUND

Field of the Disclosure

The present disclosure relates generally to treatments and preventative measures of microbially mediated disease. Such treatments and measures, as well as methods, for use therewith are provided.

Background

Periodontitis is one of the most widespread infectious diseases in adulthood, with an estimated 5-20% of the world's population suffering from generalized chronic periodontitis. Beyond the immediate effects on oral health, there is an association between periodontitis and some serious chronic diseases, such as coronary heart disease and diabetes. Chronic periodontitis is the result of a breakdown of periodontal tissue-microbe homeostasis, which then leads to uncontrolled inflammation. One thousand bacterial species can be detected in the oral cavity, and about 200 can be present in any one individual. *Porphyromonas gingivalis* appears to be a keystone pathogen and to play an important role in development of a periodontitis-provoking microbiota. *P. gingivalis*, although a low-abundance biofilm species, has been seen to significantly alter the compositions of the commensal bacteria in the mouse oral microbiota, including *Streptococcus* species. *P. gingivalis* is recruited to microbial communities by earlier colonizers, such as oral streptococci. While there is no direct evidence that earlier colonizers are associated with periodontitis, some of these organisms can provide a substratum and metabolic support for periodontal pathogens. Notably, the importance of co-aggregation or co-adhesion for the development of plaque biofilms has been demonstrated in vitro and in vivo. A well-studied interaction of earlier and later colonizers of dental plaque is co-adhesion of *Streptococcus gordonii* and *P. gingivalis*. Studies have shown involvement of multiple sets of adhesins in this process. Thus, it is likely that these specific protein-protein interactions promote *P. gingivalis* colonization on the existing biofilms consisting of *S. gordonii* and related oral streptococci.

Although less understood, antagonistic relationships are also reported between oral bacteria. *P. gingivalis*, for example, neither grows with *Streptococcus oralis* in two-species biofilms nor does it co-aggregate with *Streptococcus mutans*.

Periodontitis is caused by biofilms rather than bacteria in a planktonic state; therefore, colonization of *P. gingivalis* in dental plaque is a key step in the initiation of periodontitis. In fact, the majority of *P. gingivalis* clinical isolates are fimbriated, especially when isolated at the bottoms of periodontal pockets. Major fimbriae (long fimbriae) composed of FimA, are a well-studied virulence factor contributing to colonization, biofilm formation, cell invasion, bone resorption, and the evasion of host defense systems. Studies have shown that host immune responses invoked by *P. gingivalis* fimbriae (FimA) are initiated by recognition of, and interaction with, Toll-like receptor 2 followed by the activation of a MyD88-dependent antimicrobial pathway, a phosphatidylinositol-3 kinase (Pl3K)-dependent pro-adhesive pathway, the β2-integrin complement receptor 3 (CR3) and/or TNF-α production.

Treatments of periodontitis usually include surgical and nonsurgical mechanical therapies that sometime are supplemented by systemic or local administration of antibiotics, especially in the treatment of severe and refractory periodontitis. It appears that the adjunctive use of antibiotics may improve the results of mechanical therapies. However, meta-analyses suggest that benefits of antibiotic treatments for periodontitis have to be balanced against their side effects. Concerns for the use of antibiotics are breaking beneficial relationships between human and our commensal microbiota and emerging oral bacterial resistance to antibiotics.

Therefore there is a need for therapies that can specifically interfere with the colonization of periodontal pathogens such as *P. gingivalis* without contributing to antibiotic resistance or destroying populations of beneficial bacteria. There is also a need for approaches to interfere with pathogenicity and biofilm formation by *P. gingivalis*.

SUMMARY

It has been discovered that certain portions (but not others) of the arginine deiminase from the bacterium *Streptococcus cristatus* are useful in counter *P. gingivalis* infection. They function to prevent the formation of biofilms containing the oral pathogen *P. gingivalis* and to reduce the expression of specific virulence-associated proteins in the oral pathogen *P. gingivalis* (e.g., the major protein subunit of the short fimbriae (Mfa1, controlled by the mfa1 gene), the Gingipain R1 catalytic domain (RgpA/B), the Gingipain R1 adhesin domain (RgpA), and lysine gingipain protease (Kgp, controlled by the kgp gene)). Some of these portions are found in the C-terminal region of the protein, whereas the region responsible for the enzyme's deiminase activity is found in the N-terminal region. Others are found in the N-terminal region, despite the discovery that the N-terminal region as a whole has no activity in preventing biofilm formation.

In a first aspect, a peptide is provided for modulating biofilm formation by a bacterium, the peptide having a sequence of at least 60% identity with at least one of: SEQ ID NOS: 2-7, and wherein said peptide has no significant arginine deiminase activity.

In a second aspect, a pharmaceutical composition for treating or preventing a plaque-related condition or symptom is provided, the composition comprising a compound comprising a peptide sequence having at least 60% identity with at least one of: SEQ ID NOS: 2-7, and wherein said peptide has no significant arginine deiminase activity. In a third aspect, a method of treating or preventing a plaque-related condition or symptom in a subject is provided, the method comprising locally administering to the dental and/or gingival surfaces of the subject a therapeutically effective amount of a compound comprising a peptide sequence having at least 60% identity with at least one of: SEQ ID NOS: 2-7, and wherein said peptide has no significant arginine deiminase activity.

In a fourth aspect, a use of a compound in the manufacture of a pharmaceutical composition for treating or preventing a plaque-related condition or symptom is provided, wherein the compound comprises a peptide sequence having at least 60% identity with at least one of: SEQ ID NOS: 2-7, and wherein said peptide has no significant arginine deiminase activity.

In a fifth aspect, a method of reducing the likelihood of the formation of a biofilm containing a population of *Porphyromonas gingivalis* on a surface is provided, the method comprising exposing the surface to an effective concentration of a compound comprising a peptide sequence having at least 60% identity with at least one of: SEQ ID NOS: 2-7, and wherein said peptide has no significant arginine deiminase activity.

In a sixth aspect, a method of reducing the expression of a biofilm-associated gene in a bacterium is provided, the method comprising exposing the bacterium to an effective concentration of a compound comprising a peptide sequence having at least 60% identity with at least one of: SEQ ID NOS: 2-7, and wherein said peptide has no significant arginine deiminase activity.

In a seventh aspect, a nucleic acid is provided that encodes the peptide of the first aspect, or is complementary to a nucleic acid that encodes it.

In an eight aspect, a method of reducing the expression of a virulence-associated gene in a bacterium is provided, the method comprising exposing the bacterium to an effective concentration of a compound comprising a peptide sequence having at least 60% identity with at least one of: SEQ ID NOS: 3-7, wherein said virulence-associated gene is selected from the group consisting of the major protein subunit of the short fimbriae (mfa1), the Gingipain R1 catalytic domain (rgpA/B), the Gingipain R1 adhesin domain (rgpA), and lysine gingipain protease (kgp).

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

P. gingivalis 33277 (A) and W83 (B) were grown in TSB media in the presence or absence of P4 (24 µM). $OD_{600}$ was measured over a period of 30 h. Curves are means of triplicate samples, with error bars representing the standard deviation.

Figure 10A:
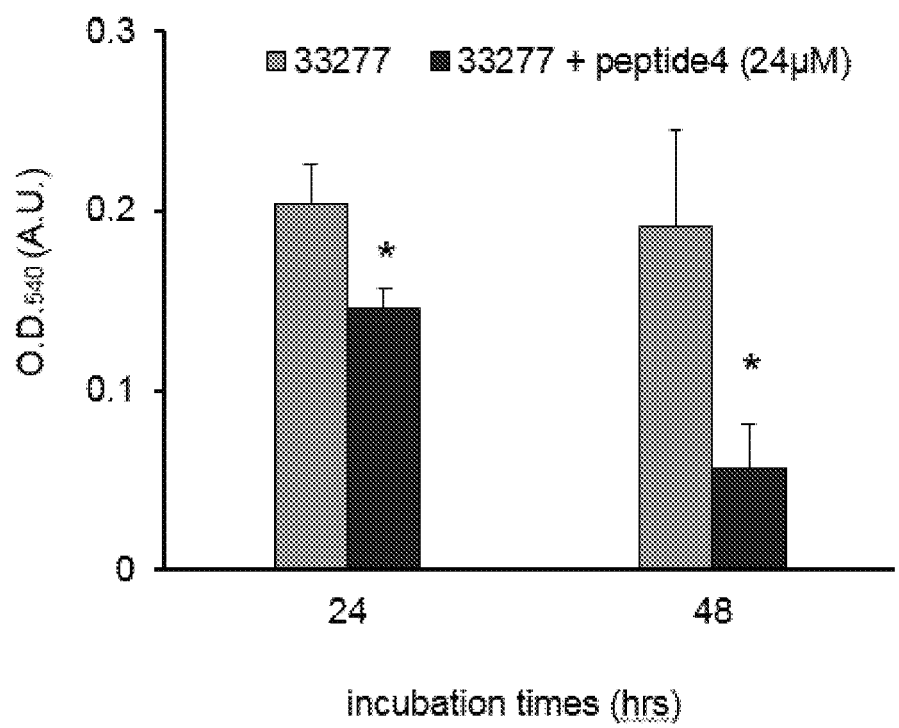
Figure 10B:
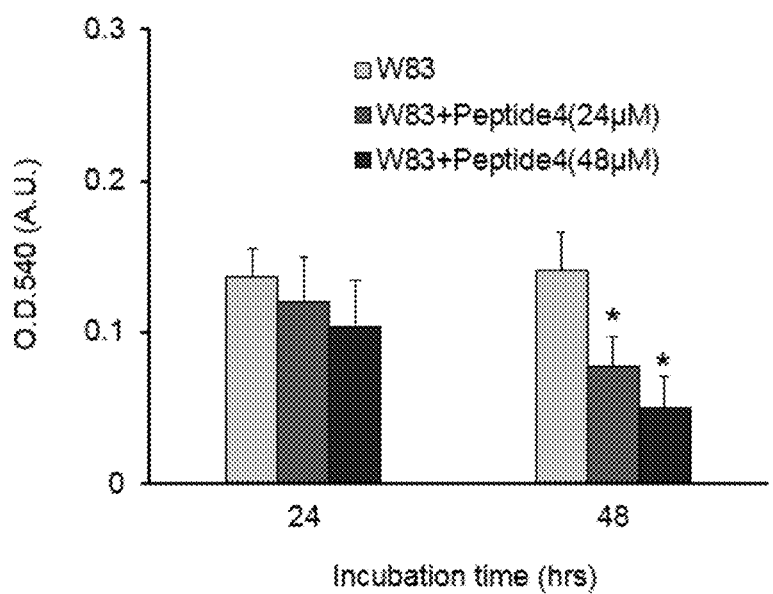

FIGS. 10A-10B show the quantitation of P. gingivalis attachment to a saliva-coated surface. Adherence assays were conducted in 96-well polystyrene microtiter plates. The wells were precoated with human whole saliva and inoculated with P. gingivalis 33277 (A) or W83 (B) grown with P4 (24 µM) or control peptide at 37° C. anaerobically. The ability of P. gingivalis to attach and form microcolonies on the surface was quantified by crystal violet staining. Each bar represents the mean±standard deviation of binding capability from three independent experiments.

Figure 11:
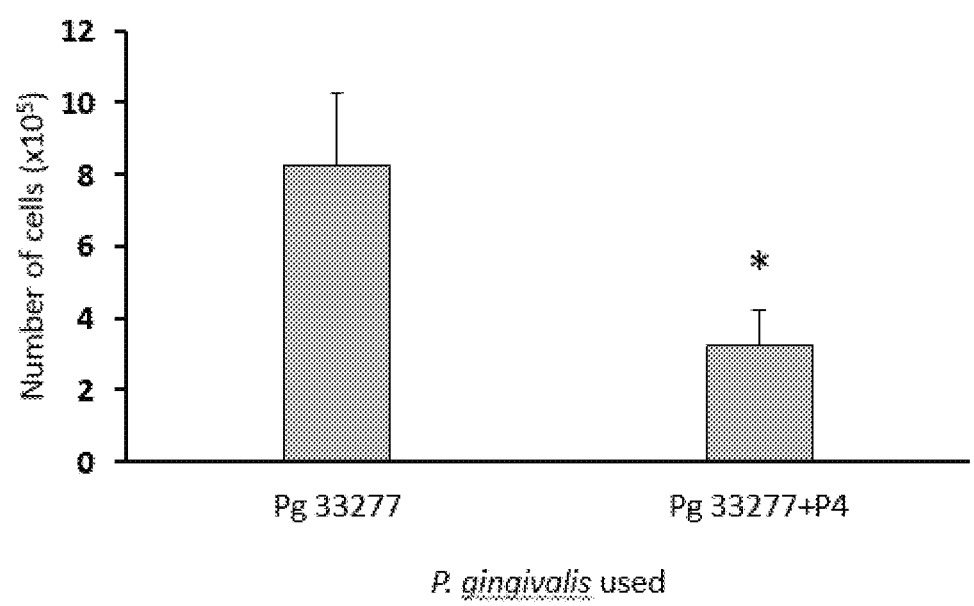

FIG. 11 shows the formation of P. gingivalis 33277-S. gordonii DL1 heterotypic biofilms. S. gordonii DL1 biofilms were established on polystyrene surfaces coated with human whole saliva. P. gingivalis 33277 grown with or without P4 (24 µM) was reacted with the DL1 biofilms for 4 h. The bound 33277 in the biofilms was quantitated using qPCR. Each bar represents the number of 33277 cells detected in the biofilms. Error bars indicate standard deviations.

FIGS. 12A-12D show the dispersion of P. gingivalis from the heterotypic biofilms by P4. P. gingivalis 33277 grown without P4 was introduced into wells of six-plates covered with S. gordonii DL1 biofilms to form the heterotypic biofilms. P4 (24 µM) was then added to the wells. The numbers of P. gingivalis cells in the growth media (A), bound on S. gordonii biofilms (B), total number of 33277 in the wells (C), and numbers of S. gordonii in the growth media (D) were determined using qPCR. Numbers of bacterial cells in the wells with or without P4 were compared, and an asterisk indicates a significant difference in numbers of P. gingivalis cells in the wells in the presence or absence of P4 (t test, $p<0.05$).

Figure 13A:
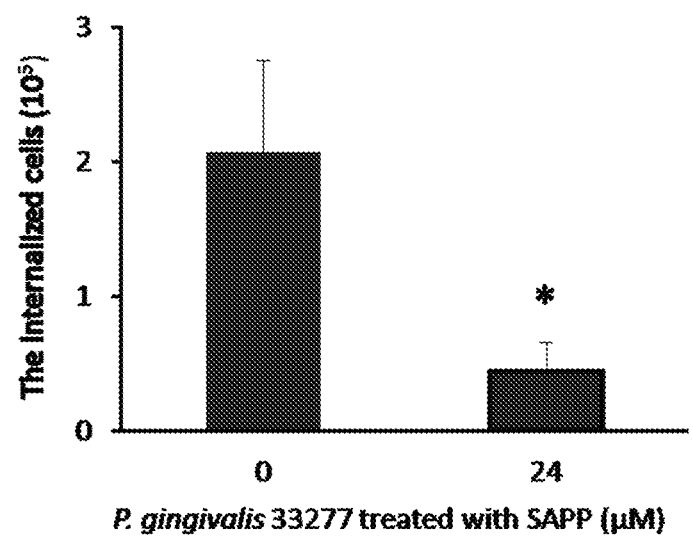
Figure 13B:
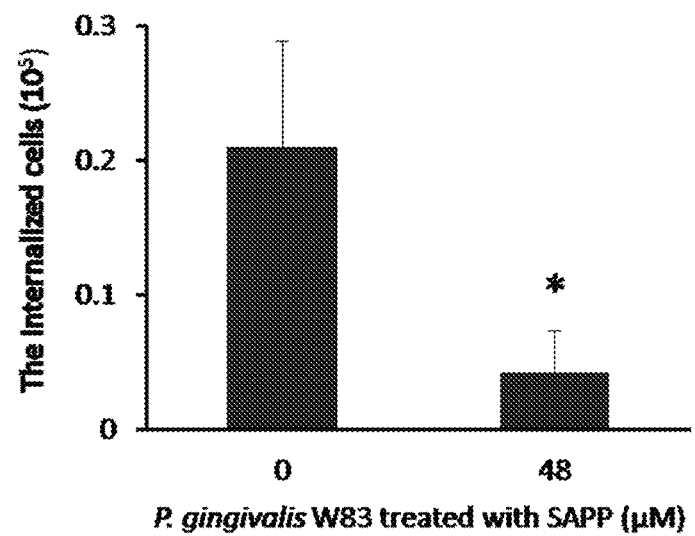

FIGS. 13A-13B show P4-mediated Inhibition of oral keratinocyte invasion by P. gingivalis. Invasion of human oral keratinocytes (HOKs) by P. gingivalis was determined by an antibiotic protection assay. P. gingivalis 33277 (A) or W83 (B) were grown with 24 or 48 µM P4, respectively. The number of internalized P. gingivalis cells was represented with means±SD of triplicates. An asterisk indicates a significant difference between invasive levels observed for P. gingivalis cells grown with or without P4 ($p<0.05$; t test).

FIGS. 14A-14D show a comparison of P. gingivalis gingipain protease activities. Rgp or Kgp activities associated with P. gingivalis cells (A-B) or in the culture media of P. gingivalis (C-D) were tested. P. gingivalis 33277 or W83 were grown with or without P4 (48 µM) for 24 h, and the bacterial cells and the growth media were separated by centrifugation. Gingipain activity of KDP128 (an $rgpA^-$, $rgpB^-$, and $kgp^-$ mutant) was evaluated, which served as a negative control. Asterisks indicate a statistical difference of protease activity levels in P. gingivalis strains grown with or without P4 ($p<0.05$; t test).

Figure 15A:
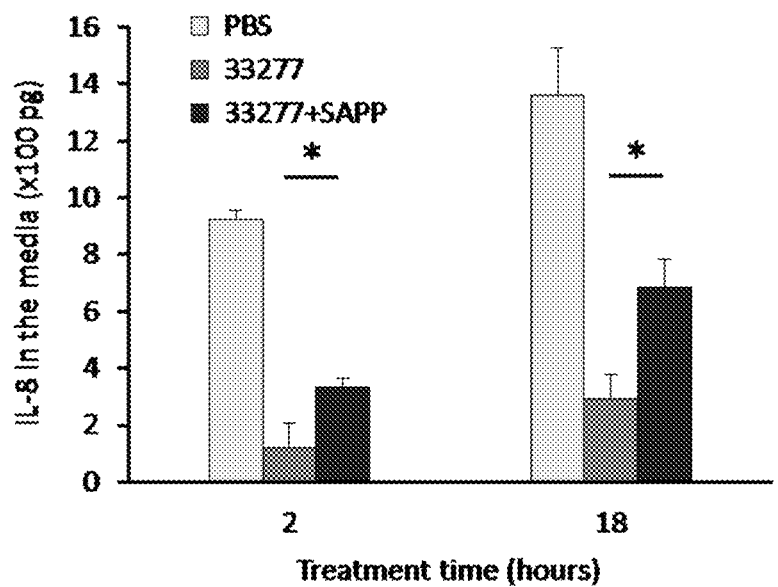
Figure 15B:
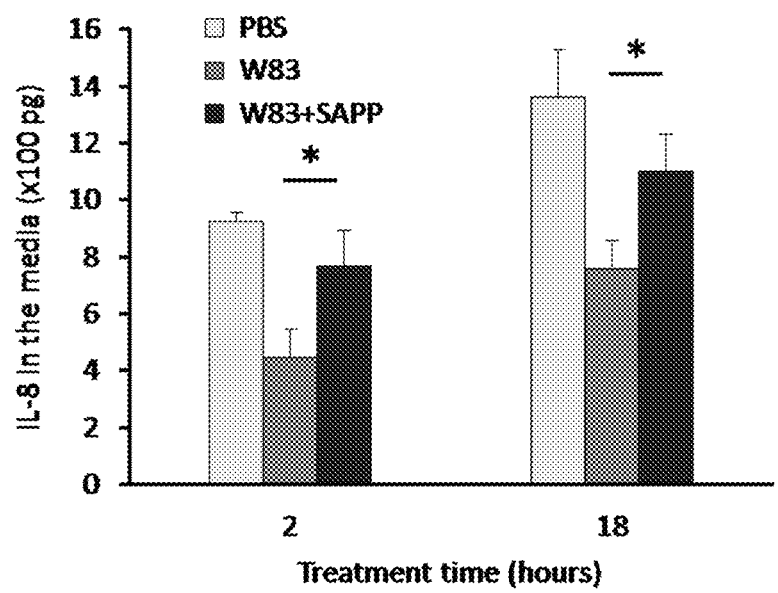

FIGS. 15A-15B shows the determination of IL-8 level in the grown media of HOKs. HOKs were exposed to P. gingivalis 33277, or W83 at a MOI of 10 for 2 and 18 h, and the culture supernatants and HOKs were collected, respectively. IL-8 levels in the culture media (a-b) were measured using an ELISArray Kit. Each bar represents means of IL-8 concentration, and standard deviations were calculated from three biological replicates. Asterisks indicate statistical difference of IL-8 concentration in the culture supernatants of HOKs treated with P. gingivalis grown with or without P4 ($p<0.05$; t-test).

DETAILED DESCRIPTION

A. Definitions

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well known functions or constructions may not be described in detail for brevity or clarity.

The terminology used herein is for the purpose of describing particular embodiments only and is not intended to be limiting. As used herein, the singular forms "a", "an" and "the" are intended to include the plural forms as well, unless the context clearly indicates otherwise.

The terms "first", "second", and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

The term "consisting essentially of" means that, in addition to the recited elements, what is claimed may also contain other elements (steps, structures, ingredients, components, etc.) that do not adversely affect the operability of what is claimed for its intended purpose as stated in this disclosure. Importantly, this term excludes such other elements that adversely affect the operability of what is claimed for its intended purpose as stated in this disclosure, even if such other elements might enhance the operability of what is claimed for some other purpose.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. For biological systems, the term "about" refers to an acceptable standard deviation of error, preferably not more than 2-fold of a given value. Numerical quantities given in this description are approximate unless stated otherwise, meaning that the term "about" or "approximately" can be inferred when not expressly stated. Numerical quantities in the claims are exact unless stated otherwise.

Terms such as "administering" or "administration" include acts such as prescribing, dispensing, giving, or taking a substance such that what is prescribed, dispensed, given, or taken actually contacts the patient's body externally or internally (or both). In embodiments of this disclosure, terms such as "administering" or "administration" include self-administering, self-administration, and the like, of a substance. Indeed, it is specifically contemplated that instructions or a prescription by a medical professional to a subject or patient to take or otherwise self-administer a substance is an act of administration.

The terms "prevention", "prevent", "preventing", "suppression", "suppress" and "suppressing" as used herein refer to a course of action (such as administering a pharmaceutical composition) initiated prior to the onset of a clinical manifestation of a disease state or condition so as to reduce the likelihood or severity. Such reduction in likelihood or severity need not be absolute to be useful.

The terms "treatment", "treat" and "treating" as used herein refers to a course of action (such as administering a pharmaceutical composition) initiated after the onset of a clinical manifestation of a disease state or condition so as to eliminate or reduce such clinical manifestation of the disease state or condition. Such treating need not be absolute to be useful.

The term "in need of treatment" as used herein refers to a judgment made by a caregiver that a patient requires or will benefit from treatment. This judgment is made based on a variety of factors that are in the realm of a caregiver's expertise, but that include the knowledge that the patient is ill, or will be ill, as the result of a condition that is treatable by a method or device of the present disclosure.

The term "in need of prevention" as used herein refers to a judgment made by a caregiver that a patient requires or will benefit from prevention. This judgment is made based on a variety of factors that are in the realm of a caregiver's expertise, but that include the knowledge that the patient will be ill or may become ill, as the result of a condition that is preventable by a method or device of the disclosure.

The term "individual", "subject" or "patient" as used herein refers to any animal, including mammals, such as mice, rats, other rodents, rabbits, dogs, cats, swine, cattle, sheep, horses, or primates, and humans. The term may specify male or female or both, or exclude male or female.

The term "therapeutically effective amount" (or simply "effective amount") as used herein refers to an amount of a compound, either alone or as a part of a pharmaceutical composition, that is capable of having any detectable, positive effect on any symptom, aspect, or characteristics of a disease state or condition. Such effect need not be absolute to be beneficial.

The term "pharmaceutically acceptable salts" as used herein includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The term "nucleotide" as used herein refers to any nucleotide, natural or synthetic. It includes conventional DNA or RNA bases (A, G, C, T, U), base analogs, e.g., inosine, 5-nitroindazole and others, imidazole-4-carboxamide, pyrimidine or purine derivatives, e.g., modified pyrimidine base 6H,8H-3,4-dihydropyrimido[4,5-c][1,2]oxazin-7-one (sometimes designated "P" base that binds A or G) and modified purine base N6-methoxy-2,6-diaminopurine (sometimes designated "K" base that binds C or T), hypoxanthine, N-4-methyl deoxyguanosine, 4-ethyl-2'-deoxycytidine, 4,6-difluorobenzimidazole and 2,4-difluorobenzene nucleoside analogues, pyrene-functionalized LNA nucleoside analogues, deaza- or aza-modified purines and pyrimidines, pyrimidines with substituents at the 5 or 6 position and purines with substituents at the 2, 6 or 8 positions, 2-aminoadenine (nA), 2-thiouracil (sU), 2-amino-6-methylaminopurine, O-6-methylguanine, 4-thio-pyrimidines, 4-amino-pyrimidines, 4-dimethylhydrazine-pyrimidines, O-4-alkyl-pyrimidines and hydrophobic nucleobases that form duplex DNA without hydrogen bonding. Nucleobases can be joined together by a variety of linkages or conformations, including phosphodiester, phosphorothioate or methylphosphonate linkages, peptide-nucleic acid linkages.

The term "polynucleotide" as used herein refers to a multimeric compound comprising nucleotides linked together to form a polymer, including conventional RNA, DNA, LNA, BNA, copolymers of any of the foregoing, and analogs thereof.

The term "nucleic acid" as used herein refers to a single stranded polynucleotide or a duplex of two polynucleotides. Such duplexes need not be annealed at all locations, and may contain gaps or overhangs.

Nucleic acids are "complementary" to each other, as used herein, when a nucleotide sequence in one strand of a nucleic acid, due to orientation of its nucleotide hydrogen atoms, hydrogen bonds to another sequence on an opposing nucleic acid strand (of course, a strand of a nucleic acid may be self-complementary as well). The complementary bases typically are, in DNA, A with T, and C with G, and, in RNA, C with G, and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not perfectly complementary to a sequence in an opposing strand, but that sufficient bonding occurs between bases on the two strands to form a stable hybrid complex at a given set of hybridization conditions (e.g., salt concentration and temperature). Such conditions can be predicted by using the sequences and standard models to predict the $T_m$ of hybridized strands, or by empirical determination of $T_m$ by using established methods. $T_m$ refers to the temperature at which a population of hybridization complexes formed between two nucleic acid strands are 50% denatured. At a temperature below the $T_m$, formation of a hybridization complex is favored, whereas at a temperature above the $T_m$, melting or separation of the strands in the hybridization complex is favored. Such stringency is based on the melting temperature ($T_m$) of the nucleic acid binding complex, as taught in Berger and Kimmel (1987, Guide to Molecular Cloning Techniques, *Methods in Enzymology,* 152, Academic Press, San Diego Calif.). The $T_m$ of an annealed duplex depends on the base composition of the duplex, the frequency of base mismatches, and the ionic strength of the reaction medium. The $T_m$ of a duplex can be calculated by those of ordinary skill in the art based on these two factors using accepted algorithms. Maximum stringency typically occurs at about 5° C. below $T_m$; high stringency at about 5-10° C. below $T_m$; intermediate stringency at about 10-20° C. below $T_m$; and low stringency at about 20-25° C. below $T_m$. As will be understood by those of skill in the art, a maximum stringency hybridization can be used to identify or detect identical nucleotide sequences while an intermediate (or low) stringency hybridization can be used to identify or detect similar or related sequences. The term "stringent" by itself in this context refers to intermediate stringency. Unless stated otherwise, any reference to complementarity in this disclosure refers to complementarity under conditions of intermediate stringency. Terms such as maximally stringent, highly stringent, and poorly stringent, refer to conditions of maximal stringency, high stringency, and low stringency respectively.

The term "peptide" refers to a polymer of two or more amino acids. The constituent amino acids may include the 20 "standard" amino acids but are not limited to them, and may include nonstandard or modified amino acids.

B. ACTIVE PORTIONS OF ARGININE DEIMINASE

It has been discovered that the certain portions of *S. cristatus* arginine deiminase can be used to influence biofilm formation by *P. gingivalis*, thus mediating many downstream morbidities that are caused directly or indirectly by this common pathogen. Compounds comprising such peptides may have downstream effects of treating and preventing periodontitis or a periodontitis-related condition or symptom in a subject. Specifically, it has been discovered that biofilm formation by *P. gingivalis* can be inhibited using compounds comprising a peptide sequence having at least 60% identity with at least one of: SEQ ID NOS: 2-7, and wherein said peptide has no significant arginine deiminase activity. Such compounds are referred to herein as "active compounds."

The sequence of *S. cristatus* arginine deiminase is believed to be:

```
                                             SEQ ID NO: 1
MSTHPIHVFS  EIGKLKKVML  HRPGKELENL  LPDYLERLLF

DDIPFLEDAQ  KEHDAFAQAL  RDEGIEVLYL  EKLAAESLIS

PEIREQFIEE  YLEEANIRGR  ETKKAIRELL  HGIKDNQELV

EKTMAGVQKA  ELPEIPDEAK  GLTDLVESDY  PFAIDPMPNL

YFTRDPFATI  GNAVSLNHMF  ADTRNRETLY  GKYIFKYHPE

YAGKVELVYN  REEDTRIEGG  DELVLSKDVL  AVGISQRTDA

ASIEKLLVNI  FKKNVGFKKV  LAFEFANNRK  FMHLDTVFTM

VDYDKFTIHP  EIEGDLRVYS  VTYENEKLKI  VEEKGDLAEL

LAQNLGVEKV  HLIRCGGGNI  VAAGREQWND  GSNTLTIAPG

VVVVYDRNTV  TNKILEEYGL  RLIKIRGSEL  VRGRGGPRCM

SMPEREEV
```

The C-terminal domain is underlined (SEQ ID NO: 2). Some embodiments of the peptide are related to (i.e., have at least 60% identity with) portions of the C-terminal domain, which has been observed to affect the fimA expression of *P. gingivalis* when present as a 208 amino acid portion. It has also been observed that the C-terminal domain does not have any deiminase activity. Further embodiments of the peptide are related to smaller portions of the C-terminal domain. Specific embodiments of the peptide are related to at least one of the following portions of the C-terminal domain that have been demonstrated to bind to *P. gingivalis* surface proteins: VYNREEDTRIEGGDEL (SEQ ID NO: 5), NIFKKNVGFKK (SEQ ID NO: 6), and ELVRGRGGPRCMSMPF (SEQ ID NO: 7). Note that structural modeling suggests that in the native protein SEQ ID NO: 6 is at the end of an α-helix that is followed by a few random coil residues that it in turn followed by a β-sheet. Consequently some embodiments of the peptide comprise a sequence related to SEQ ID NO: 6 flanked by 4-8 residues on the N-terminal end and the C-terminal end.

Some embodiments of the peptide are related to portions of the N-terminal domain. Although the N-terminal domain as a whole does not appear to affect the fimA expression of *P. gingivalis*, smaller portions have been demonstrated to bind to *P. gingivalis* surface proteins. Specific examples of such smaller portions include IRGRETKK (SEQ ID NO: 3) and NHMFADTRNRE (SEQ ID NO: 4).

The size of the peptide may be varied according to the specific needs of the application. For example, varying the size of the peptide can adjust its solubility, protease resistance, and isoelectric point (pI). Some embodiments of the peptide are about 5-208 amino acids long; further embodiments of the peptide are no more than 200, 190, 180, 170, 160, 150, 140, 130, 120, 110, 100, 90, 80, 70, 60, 50, 40, 30, 20, 16, 15, 14, 13, 12, 11, 10, 9, 8, 7, 6, or 5 amino acids long.

The level of identity of the peptide sequence may be at least 60%. In further embodiments the level of identity is at least 70%, 75%, 80%, 85%, 90%, 95%, 97.5%, 98%, 99%, 99.9%, 99.99%, or 100%.

A skilled artisan will be able to determine suitable variants of SEQ ID NOS: 2-7. For example, even in relatively conserved regions, one may substitute chemically similar amino acids for the native residues while retaining activity (conservative amino acid residue substitutions). Therefore, even areas that may be important for biological activity or for structure may be subject to conservative amino acid substitutions without destroying the biological activity or without adversely affecting the peptide structure.

Conservative modifications to the amino acid sequence any of SEQ ID NOS: 2-7 (and the corresponding modifications to the encoding nucleotides) will produce a peptide derivative having functional and chemical characteristics similar to those of the native sequence. In contrast, substantial modifications in the functional and/or chemical characteristics of SEQ ID NOS: 2-7 may be accomplished by selecting substitutions which differ significantly in their effect on maintaining the structure of the molecular backbone in the area of the substitution.

For example, a "conservative amino acid substitution" may involve a substitution of a native amino acid residue with a non-native residue such that there is little or no effect on the polarity or charge of the amino acid residue at that position. Furthermore, any native residue in the polypeptide may also be substituted with alanine.

Conservative amino acid substitutions also encompass non-naturally occurring amino acid residues which are typically incorporated by chemical peptide synthesis rather than by synthesis in biological systems. These include peptidomimetics, and other reversed or inverted forms of amino acid moieties. It will be appreciated by those of skill in the art that nucleic acid and polypeptide molecules described herein may be chemically synthesized as well as produced by recombinant means.

Naturally occurring residues may be divided into classes based on common side chain properties: 1) hydrophobic: norleucine, Met, Ala, Val, Leu, Ile; 2) neutral hydrophilic: Cys, Ser, Thr, Asn, Gln; 3) acidic: Asp, Glu; 4) basic: His, Lys, Arg; 5) residues that influence chain orientation: Gly, Pro; and 6) aromatic: Trp, Tyr, Phe.

For example, non-conservative substitutions may involve the exchange of a member of one of these classes for a member from another class. Such substituted residues may be introduced into regions of SEQ ID NOS: 2-7 that are homologous with SEQ ID NOS: 2-7 orthologs, or into the non-homologous regions of the molecule.

In making such changes, the hydropathic index of amino acids may be considered. Each amino acid has been assigned a hydropathic index on the basis of their hydrophobicity and charge characteristics, these are:

isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (Kyte et al., *J. Mol. Biol.*, 157:105-131, 1982). It is known that certain amino acids may be substituted for other amino acids having a similar hydropathic index or score and still retain a similar biological activity.

In making changes based upon the hydropathic index, the substitution of amino acids whose hydropathic indices are within +/− 2 may be used; in an alternate embodiment, the hydropathic indices are with +/− 1; in yet another alternate embodiment, the hydropathic indices are within +− 0.5.

It is also understood in the art that the substitution of like amino acids can be made effectively on the basis of hydrophilicity. The greatest local average hydrophilicity of a polypeptide as governed by the hydrophilicity of its adjacent amino acids, correlates with a biological property of the protein.

The following hydrophilicity values have been assigned to amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within +/− 2 may be used; in an alternate embodiment, the hydrophilicity values are with +/− 1; in yet another alternate embodiment, the hydrophilicity values are within +/− 0.5.

The substitutions may be made to increase or decrease the solubility of the peptide. For example, the substitution of non-essential hydrophobic amino acids with amino acids that are charged or polar will tend to improve solubility. Substitutions may also be made to reduce the rate of biodegradation of the peptide, for example by substituting non-essential amino acids with non-natural amino acids.

Desired amino acid substitutions (whether conservative or non-conservative) can be determined by those skilled in the art at the time such substitutions are desired. For example, amino acid substitutions can be used to identify important residues of the Angptl4 polypeptide, or to increase or decrease the affinity of the SEQ ID NOS: 2-7 with a particular binding target in order to increase or decrease activity.

Exemplary amino acid substitutions are set forth in TABLE 1.

TABLE 1

Amino Acid Substitutions

| Original Amino Acid | Exemplary substitution | Preferred substitution |
| --- | --- | --- |
| Ala | Val, Leu, Ile | Val |
| Arg | Lys, Gln, Asn | Lys |
| Asn | Glu | Glu |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Ile, Val, Met, Ala, Phe, Norleucine | Ile |
| Lys | Arg, 1,4-diaminobutyric acid, Gln, Asn | Arg |
| Met | Leu, Phe, Ile | Leu |
| Phe | Leu, Val, Ile, Ala, Tyr | Leu |
| Pro | Ala, Gly | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

Additionally, one skilled in the art can review structure-function studies identifying residues in similar polypeptides that are important for activity or structure. In view of such a comparison, one can predict the importance of amino acid residues in SEQ ID NOS: 2-7 that correspond to amino acid residues that are important for activity or structure in similar polypeptides. One skilled in the art may opt for chemically similar amino acid substitutions for such predicted important amino acid residues of SEQ ID NOS: 2-7.

One skilled in the art can also analyze the three-dimensional structure and amino acid sequence in relation to that structure in similar polypeptides. In view of that information, one skilled in the art may predict the alignment of amino acid residues of SEQ ID NOS: 2-7 with respect to its three dimensional structure. One skilled in the art may choose not to make radical changes to amino acid residues predicted to be on the surface of the protein, since such residues may be involved in important interactions with other molecules. Moreover, one skilled in the art may generate test SEQ ID NOS: 2-7 derivatives containing a single amino acid substitution at each desired amino acid residue. The derivatives can then be screened using activity assays known to those skilled in the art and as disclosed herein. Such derivatives could be used to gather information about suitable substitution. For example, if one discovered that a change to a particular amino acid residue resulted in destroyed, undesirably reduced, or unsuitable activity, derivatives with such a change would be avoided. In other words, based on information gathered from such routine experiments, one skilled in the art can readily determine the amino acids where further substitutions should be avoided either alone or in combination with other mutations.

Numerous scientific publications have been devoted to the prediction of secondary structure from analyses of amino acid sequences (see Chou et al., *Biochemistry*, 13(2):222-245, 1974; Chou et al., *Biochemistry*, 113(2):211-222, 1974; Chou et al., *Adv. Enzymol. Relat. Areas Mol. Biol.*, 47:45-148, 1978; Chou et al., *Ann. Rev. Biochem.*, 47:251-276, 1979; and Chou et al., *Biophys. J.*, 26:367-384, 1979). Moreover, computer programs are currently available to assist with predicting secondary structure of polypeptides. Examples include those programs based upon the Jameson-Wolf analysis (Jameson et al., *Comput. Appl. Biosci.*, 4(1): 181-186, 1998; and Wolf et al., *Comput. Appl. Biosci.*, 4(1):187-191; 1988), the program PepPlot.®. (Brutlag et al., *CABS*, 6:237-245, 1990; and Weinberger et al., *Science*, 228:740-742, 1985), and other new programs for protein tertiary structure prediction (Fetrow et al., *Biotechnology*, 11:479-483, 1993).

Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural data base (PDB) has provided enhanced predictability of secondary structure, including the potential number of folds within a polypeptide's or protein's structure (see Holm et al., *Nucl. Acid. Res.*, 27(1):244-247, 1999).

Additional methods of predicting secondary structure include "threading" (Jones, D., *Curr. Opin. Struct. Biol.*, 7(3):377-87, 1997; Suppl et al., Structure, 4(1):15-9, 1996), "profile analysis" (Bowie et al., *Science*, 253:164-170, 1991; Gribskov et al., *Meth. Enzym.*, 183:146-159, 1990; and Gribskov et al., *Proc. Nat. Acad. Sci.*, 84(13): 4355-4358, 1987), and "evolutionary linkage" (See Home, supra, and Brenner, supra).

Any of the polypeptide forms discussed herein may also contain a sequence useful in the identification or purification of the polypeptide; an example of such a sequence is the C-terminal V5 tag. The foregoing also includes nucleic acid sequences (such as, but not limited to cDNA sequences) coding for such polypeptides, including polypeptide derivatives as described herein. Examples of such nucleic acids include those encoding the polypeptides of SEQ ID NOS: 1-7. These can include nucleic acids comprising the sequence of any one of SEQ ID NOS: 8 (encoding SEQ ID NO: 1), 9 (encoding SEQ ID NO: 2), 10 (encoding SEQ ID NO: 3), 11 (encoding SEQ ID NO: 4), 12 (encoding SEQ ID NO: 5), 13 (encoding SEQ ID NO: 6), and 14 (encoding SEQ ID NO: 7).

C. PHARMACEUTICAL COMPOSITIONS

A pharmaceutical composition for treating or preventing a plaque-related condition or symptom is provided, the composition comprising any of the active compounds provided above. The compositions disclosed may comprise one or more of such active compounds, in combination with a pharmaceutically acceptable carrier. Examples of such carriers and methods of formulation may be found in Remington: The Science and Practice of Pharmacy (20th Ed., Lippincott, Williams & Wilkins, Daniel Limmer, editor), and are generally well understood by those skilled in the art. To form a pharmaceutically acceptable composition suitable for administration, such compositions will contain a therapeutically effective amount of an active compound.

The pharmaceutical compositions of the disclosure may be used in the treatment and prevention methods of the present disclosure. Such compositions are administered to a subject in amounts sufficient to deliver a therapeutically effective amount of the active compound so as to be effective in the treatment and prevention methods disclosed herein. The therapeutically effective amount may vary according to a variety of factors such as the subject's condition, weight, sex and age. For example, some embodiments of the composition comprise up to the median lethal dose (LD50) of the active compound. The LD50 can be ascertained using standard toxicological methods, or by reference to past studies. Alternatively, the pharmaceutical composition may be formulated to achieve a desired concentration of the active compound at the dental and/or gingival surfaces of the subject.

Other factors include the mode and site of administration. The pharmaceutical compositions may be formulated to be provided to the subject in any method known in the art. Exemplary dosage forms include subcutaneous, intravenous, topical, epicutaneous, oral, intraosseous, intramuscular, intranasal and pulmonary. The compositions of the present disclosure may be formulated to be administered only once to the subject or more than once to the subject. Furthermore, when the compositions are administered to the subject more than once, a variety of regimens may be used, such as once per day, once per week, once per month or once per year. The compositions may also be formulated to be administered to the subject more than one time per day. The therapeutically effective amount of the active compound and appropriate dosing regimens may be identified by testing in order to obtain optimal activity, while minimizing any potential side effects. In addition, formulation for co-administration or sequential administration of other agents may be desirable.

The compositions of the present disclosure may be formulated to be administered systemically, such as by intravenous administration, or locally such as by subcutaneous injection or by application of a gel, fiber, paste or cream.

The compositions of the present disclosure may further comprise agents which improve the solubility, half-life, absorption, etc. of the active compound. Furthermore, the compositions of the present disclosure may further comprise agents that attenuate undesirable side effects and/or decrease the toxicity of the active compound. Examples of such agents are described in a variety of texts, such as Remington: The Science and Practice of Pharmacy (20th Ed., Lippincott, Williams & Wilkins, Daniel Limmer, editor).

The compositions of the present disclosure can be formulated in a wide variety of dosage forms for administration. For example, the compositions can be in the form of tablets, capsules, sachets, lozenges, troches, pills, powders, granules, elixirs, tinctures, solutions, suspensions, syrups, ointments, creams, pastes, emulsions, or solutions for intravenous administration or injection. Other dosage forms include for administration transdermally, via patch mechanism or ointment. Further dosage forms include formulations suitable for delivery by nebulizers or metered dose inhalers. Any of the foregoing may be modified to provide for timed release and/or sustained release formulations.

In the present disclosure, the pharmaceutical compositions may further comprise a pharmaceutically acceptable carrier. Such carriers may include vehicles, adjuvants, surfactants, suspending agents, emulsifying agents, inert fillers, diluents, excipients, wetting agents, binders, lubricants, buffering agents, disintegrating agents and carriers, as well as accessory agents, such as coloring agents and flavoring agents (collectively referred to herein as a carrier). Typically, the pharmaceutically acceptable carrier is chemically inert to the active compounds and has no detrimental side effects or toxicity under the conditions of use. The pharmaceutically acceptable carriers can include polymers and polymer matrices. The nature of the pharmaceutically acceptable carrier may differ depending on the particular dosage form employed and other characteristics of the composition.

For instance, compositions for oral administration in solid form, such as tablets, capsules, sachets, lozenges, troches, pills, powders, or granules, the active compound may be combined with an oral, non-toxic pharmaceutically acceptable inert carrier, such as inert fillers, suitable binders, lubricants, disintegrating agents and accessory agents. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, and the like. Disintegrators include, without limitation, starch, methyl cellulose, agar, bentonite, xanthum gum and the like. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid as well as the other carriers described herein. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, and gels containing, in addition to the active ingredient, such carriers as are known in the art.

The pharmaceutical composition may be a dentifrice. Dentifrices have the advantage of being widely available to consumers. People are therefore familiar with the use of dentifrices, and in most societies apply a dentifrice at least once daily as part of an oral hygiene regimen. In addition, dentifrices are effective for the local delivery of active compounds to dental and/or gingival surfaces.

The dentifrice may be selected from a group consisting of a paste, a gel, a mouthwash, a powder, and a tooth soap. In some embodiments of the composition, the dentifrice is a paste or gel comprising at least one of an abrasive, a surfactant, a humectant, and a thickener. Such abrasives include hydrated silica, dicalcium phosphate dihydrate, calcium carbonate, sodium bicarbonate, calcium pyrophosphate, and alumina. Such surfactants include sodium lauryl sulfate, sodium N-lauryl sarcosinate, pluronics, sodium lauryl sulfoacetate. Such anticaries agents include fluoride. Such tartar control ingredients include tetrasodium pyrophosphate, Gantrez S-70, sodium tripolyphosphate, and methyl vinyl ether/maleic anhydride copolymer. The dentifrice may further comprise one or more of: water; pH buffers; humectants (to prevent dry-out and increase pleasant mouth feel) such as, glycerin, sorbitol, polypropylene glycol, xylitol, and polyethylene glycol; thickeners such as silica thickeners, sodium aluminum silicates, and clays; gums such as sodium carboxymethyl cellulose, cellulose ethers, xantham gum, carrageenans, sodium alginate, and carbopols; antibacterial agents; flavoring agents such as, water-insoluble essential oils; sweetening agents such as, saccharin, dextrose, levulose, cyclamate, aspartate; coloring agents; and binders to provide consistency and shape.

For oral administration by mouthwash, the active compound may be combined with one or more of: water and alcohol (such as ethyl alcohol). The mouthwash may further comprise one or more of: surfactants, tartar control ingredients, anticaries agents, buffers, humectants, antibacterial agents, flavoring agents, and coloring agents as described in the preceding section.

In a specific embodiment, the dentifrice is a powder comprising any of the abrasives described above. The powder may further comprise any of the dry components provided above as suitable in a toothpaste. In another specific embodiment, the dentifrice is a tooth soap comprising one or more of oil and water. The oil may be any that is known to be suitable in a tooth soap, such as olive oil, coconut oil, an essential oil, and peppermint oil.

The pharmaceutical composition may be a chewing gum. The gum may comprise the active compound and a gum, such as butadiene-based synthetic rubber, birch bark tar, chicle, mastic gum, spruce gum, paraffin wax, tolu resin, styrene-butadiene rubber, isobutylene, isoprene copolymer, and petroleum wax. The gum will be present at a concentration sufficient to confer the requisite chewiness to the chewing gum, as could be formulated by one skilled in the art. Flavorings may be added, including those listed above.

The composition may be also be in oral liquid form, such as a tincture, solution, suspension, elixir and syrup; and the active compounds of the present disclosure can be dissolved in diluents, such as water, saline, or alcohols. Furthermore, the oral liquid forms may comprise suitably flavored suspending or dispersing agents such as synthetic and natural gums, for example, tragacanth, acacia, methylcellulose and the like. Moreover, when desired or necessary, suitable coloring agents or other accessory agents can also be incorporated into the mixture. Other dispersing agents that may be employed include glycerin and the like.

Formulations suitable for parenteral administration include aqueous and non-aqueous, isotonic sterile injection solutions, which can contain anti-oxidants, buffers, bacteriostats, and solutes that render the formulation isotonic with the blood of the patient, and aqueous and non-aqueous sterile suspensions that can include suspending agents, solubilizers, thickening agents, stabilizers, and preservatives. The composition may comprise a physiologically acceptable diluent, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap, an oil or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations and in the dentifrice, include petroleum, animal, vegetable, or synthetic oils. Specific examples of oils include peanut, soybean, sesame, cottonseed, corn, olive, petrolatum, and mineral. Suitable fatty acids for use in parenteral formulations include polyethylene sorbitan fatty acid esters, such as sorbitan monooleate and the high molecular weight adducts of ethylene oxide with a hydrophobic base, formed by the condensation of propylene oxide with propylene glycol, oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include: (a) cationic detergents such as, for example, dimethyldialkylammonium halides, and alkylpyridinium halides; (b) anionic detergents such as, for example, alkyl, aryl, and olefin sulfonates, alkyl, olefin, ether, and monoglyceride sulfates, and sulfosuccinates; (c) nonionic detergents such as, for example, fatty amine oxides, fatty acid alkanolamides, and polyoxyethylene polypropylene copolymers; (d) amphoteric detergents such as, for example, alkylbeta-aminopropionates, and 2-alkylimidazoline quaternary ammonium salts; and (e) mixtures thereof.

Suitable preservatives and buffers can be used in such formulations. In order to minimize or eliminate irritation at the site of injection, such compositions may contain one or more nonionic surfactants having a hydrophile-lipophile balance (HLB) of from about 12 to about 17.

Topical dosage forms, such as ointments, creams, pastes, and emulsions, containing the active compound, can be admixed with a variety of carrier materials well known in the art, such as, e.g., alcohols, aloe vera gel, allantoin, glycerine, vitamin A and E oils, mineral oil, PPG2 myristyl propionate, and the like, to form alcoholic solutions, topical cleansers, cleansing creams, skin gels, skin lotions, and shampoos in cream or gel formulations. Inclusion of a skin exfoliant or dermal abrasive preparation may also be used. Such topical preparations may be applied to a patch, bandage or dressing for transdermal delivery, or may be applied to a bandage or dressing for delivery directly to the site of a wound or cutaneous injury.

The active compounds of the present disclosure can also be formulated to be administered in the form of liposome delivery systems, such as small unilamellar vesicles, large unilamellar vesicles and antiemtrics. Liposomes can be formed from a variety of phospholipids, such as cholesterol, stearylamine or phosphatidylcholines. Such liposomes may also contain monoclonal antibodies to direct delivery of the liposome to a particular cell type or group of cell types.

The active compounds of the present disclosure may also be coupled with soluble polymers as targetable drug carriers. Such polymers can include polyvinyl-pyrrolidone, pyran copolymer, polyhydroxypropylmethacryl-amidephenol, polyhydroxyethylaspartamidephenol, or polyethyl-eneoxidepolylysine substituted with palmitoyl residues. Furthermore, the active compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

D. METHODS OF TREATMENT AND PREVENTION

A method of treating or preventing a plaque-related condition or symptom in a subject is provided, the method comprising locally administering to the dental and/or gingival surfaces of the subject a therapeutically effective amount of any of the active agents described above. Plaque biofilms inhabited by *P. gingivalis* tend to be highly virulent, resulting in high rates of dental and gum disease (such as gingivitis, and periodontitis). Periodontitis associated with *P. gingivalis* can in turn result in serious systemic disease states, including atherosclerosis, human immunodeficiency virus (HIV) disease, tooth loss, coronary artery disease, stroke, premature birth, low birth weight, poorly controlled diabetes, respiratory problems, rheumatoid arthritis, and asthma.

The method of treatment and/or prevention comprises administering to the subject the active compound in an amount sufficient to treat or prevent plaque or a plaque-related condition or symptom (therapeutically effective amount). The method will often further comprise identifying a subject in need of such treatment or prevention. Too little active compound would fail to provide the therapeutic effect. On the other hand, excessive active compound could lead to undesired side-effects.

The therapeutically effective amount may vary according to a variety of factors such as the subject's condition, weight, sex and age. For example, some embodiments of the method comprise administration of up to the median lethal dose (LD50) of the active compound. Further embodiments comprise administration of up to 50%, 25%, 10%, 1%, 0.1%, or 0.01% of the LD50. The LD50 can be ascertained using standard toxicological methods, or by reference to past studies. Alternatively, the method may comprise delivering a desired concentration of the active compound to the dental and/or gingival surfaces of the subject.

If, after the administration of the active compound, the subject still has periodontitis or a periodontitis-related condition or symptom, or is at risk for the same, then an optional step of the method is to continue administration of the active compound or pharmaceutical composition.

In one embodiment, the method comprises delivering the active compound to the dental and/or gingival surfaces of the subject. It is desirable to deliver the active compound to the dental and/or gingival surfaces because this is the site of plaque formation by *P. gingivalis*. The presence of the active compound on the dental and/or gingival surfaces is necessary to prevent formation of plaque there. Targeted delivery to the dental and/or gingival surfaces could also prevent unwanted effects on other tissues or organs. In an alternate embodiment, the method comprises administering the active compound locally to the subject's mouth. It is desirable to administer the active compound to the subject's mouth because the dental and/or gingival surfaces are in the subject's mouth. A specific embodiment comprises administering the active compound locally to the subject's mouth in which the active compound is administered in a dentifrice or gum. A dentifrice or gum containing active compound would be useful to treat or prevent plaque or a plaque-related condition or symptom because these formulations might also contain additives to improve overall oral health (e.g., fluoride). Human subjects likely already use similar formulations for routine oral hygiene, so subjects would be more likely to comply with the treatment regimen, leading to better outcomes.

E. METHODS OF REDUCING BIOFILMS

A method of reducing the likelihood of the formation of a biofilm containing a population of *P. gingivalis* on a surface is provided, the method comprising exposing the surface to an effective concentration of any of the active agents described above.

F. METHODS OF REDUCING THE EXPRESSION OF VIRULENCE GENES

It has been discovered that the expression of fimbrillin genes, mfa1, rgpA/B, rgpA, and kgp may be inhibited using the compounds disclosed above comprising specific fragments of the ArcA protein from *S. cristatus*. These genes are known to participate in biofilm formation and virulence in *P. gingivalis*. A method of reducing the expression of a biofilm or virulence-associated gene in a bacterium is provided, the method comprising exposing the bacterium to an effective concentration of any of the active compounds described above. Contact may occur in vitro or in vivo. Examples of biofilm-associated genes are fimbrillin genes (e.g., major fimbrium subunit fimA). Examples of virulence genes in *P. gingivalis* include gingipain genes, such as mfa1, rgpA/B, rgpA, and kgp. In a specific embodiment of the method the bacterium is *P. gingivalis*. The effective concentration may be determined empirically through exposure of the bacterium to varying concentrations of the active agent. In a specific embodiment of the method the concentration is 15 µM.

G. NUCLEIC ACIDS

Nucleic acids are provided that encode any of the peptides described as useful in the active agent. Such nucleic acids find use in various applications, such as expression of the peptides, genetic transfer, and gene therapy. A general embodiment of the nucleic acid comprises a coding region that encodes the peptide. An alternative general embodiment of the nucleic acid comprises a coding region that is complementary to a sequence that encodes the peptide. The complementary region may be perfectly complementary to the sequence that encodes the peptide, or it may hybridize with the sequence that encodes the peptide under conditions of maximum, high, intermediate, or poor stringency. The nucleic acid may further comprise one or more regulatory regions operatively coupled with the coding region, such as a promoter, an enhancer, a repressor binding region, or a silencer. In some embodiments of the nucleic acid, the promoter is immediately upstream (in the 5' direction) of the coding region. In a specific embodiment of the nucleic acid the promoter is a constitutive promoter.

A cell comprising any of the nucleic acids disclosed above is also provided. The cell may find utility for example in the production of the polypeptide for subsequent isolation or analysis. The cell might also be the cell of the subject that has undergone gene therapy. The cell may be a unicellular organism or a cell of a multicellular organism. Many unicellular organisms have the advantage of being easier to culture in vitro than cells from multicellular organisms. In some embodiments, the cell is a unicellular eukaryotic organism. Unicellular eukaryotic organisms suitable for the method include fungi and protists. Unicellular organisms are particularly useful in cloning, replicating, and maintaining nucleic acids of interest. Model unicellular organisms that are commonly used for this purpose include yeasts, other fungi, bacteria, protists, and archaea. Specific model organisms are well known in the art, and include bacteria such as *Escherichia coli*, *Salmonella typhimurium*, *Pseudomonas fluorescens*, *Bacillus subtilis*, *Mycoplasma genitalium*, and various *Synechocystis* sp.; protists such as *Dictyostelium discoideum*, *Tetrahymena thermophila*, *Emiliania huxleyi*, and *Thalassiosira pseudonana*; and fungi such as *Aspergillus* sp., *Neurospora crassa*, *Saccharomyces cerevisiae*, and *Schizosaccharomyces pombe*.

In some embodiments of the cell, the cell is an animal cell. Animal cell culture methods are known in the art, and those skilled in the art can develop cell culture methods suitable to the type of animal cell without undue experimentation. Animal cells have the advantage of reacting closely as would animal tissues in vivo. The animal cell may be, for example, a cell from a bird, a mammal, a mouse, a Norway rat, a cotton rat, a gerbil, a cavy, a hamster, another rodent, a rabbit, a dog, a cat, a swine, a bovine, a sheep, a goat, a horse, a domestic fowl, a primate, and a human. The cell may be present in monoculture, or with more than one type of cell in co-culture.

A vector is also provided, comprising any of the nucleic acids disclosed above. Many suitable vectors are known in the art, such as viruses, plasmids, cosmids, fosmids, phagmids, artificial chromosomes, yeast artificial chromosomes, human artificial chromosomes, plant transformation vectors, and liposomes.

H. EXAMPLES

Working Example 1

Identification of *Streptococcus cristatus* Peptides that Bind to Surface Proteins in *Porphyromonas gingivalis*

An antagonistic relationship between *Streptococcus cristatus* and *P. gingivalis* has been hypothesized, and arginine deiminase (ArcA) of *S. cristatus* is a proposed signaling molecule to which *P. gingivalis* responds by repressing the expression and production of FimA protein. Here it is demonstrated that direct interaction between *P. gingivalis* and *S. cristatus* is necessary for the cell-cell communication. Two surface proteins of *P. gingivalis*, PGN_0294 and PGN_0806, were found to interact with *S. cristatus* ArcA. Using a peptide array analysis, several *P. gingivalis*-binding sites of ArcA were identified, which led to the discovery of an 11-mer peptide with the native sequence of ArcA that repressed expression of fimbriae and of gingipains. These data indicate that a functional motif of ArcA is sufficient to selectively alter virulence gene expression in *P. gingivalis*, and PGN_0294 and PGN_0806 may serve as receptors for ArcA. These findings provide a molecular basis for future rational design of agents that interfere with the initiation and formation of a *P. gingivalis*-induced pathogenic community.

Methods

Bacterial strains and growth conditions. *P. gingivalis* strains and *A. actinomycetemcomitans* Y4 were grown from frozen stocks in Trypticase soy broth (TSB) or on TSB blood agar plates supplemented with yeast extract (1 mg/ml), hemin (5 µg/ml), and menadione (1 µg/ml), and incubated at 37° C. in an anaerobic chamber (85% N2, 10% H2, 5% CO2). *S. cristatus* CC5A and isogenic ΔarcA16 were grown in Trypticase peptone broth (TPB) supplemented with 0.5% glucose at 37° C. under aerobic conditions. Erythromycin (5 µg/ml) or tetracycline (0.5 µg/ml) were added to growth media when appropriate.

Transwell co-culture assay. *P. gingivalis* cells ($10^5$) were inoculated in each well of a six well plate, and *S. cristatus* CC5A or its arcA mutant ($10^7$) was added into the transwell inserts with a polycarbonate porous membrane of pore size 0.4 µm or 8 µm. After 16 h growth, the bacterial cells in each well of the plate were collected by centrifugation. To determine the number of CC5A migrated to the lower wells, the bacteria in the lower wells were harvested by centrifugation, and DNA was released by boiling the samples for 20 mins. Numbers of bacteria were determined by qPCR using specific primers for CC5A arcA and 33277 16s-rRNA (TABLE 2). *P. gingivalis* RNA was purified using an RNeasy mini spin column which selectively lyses *P. gingivalis* cells and not *S. cristatus* cells. Expression of the fimA gene in *P. gingivalis* was measured using real time qRT-PCR (see below).

RNA isolation and qPCR. *P. gingivalis* were homogenized in Trizol Reagent (Invitrogen, Carlsbad, Calif.) and RNA was purified using an RNeasy mini spin column (Qiagen, Valencia, Calif.). RNA samples were digested on-column with RNase-free DNase, and total RNA was tested using an Agilent 2100 Bioanalyzer to ensure the quality of the samples. Primers are listed in TABLE 2. Amplification reactions consisted of a reverse transcription using a Bio-Rad iScript Reverse Transcription Supermix on a TC-3000 thermal cycler (Techne, Staffordshire, ST15 OSA, UK) and a real-time qRT-PCR analysis using a QuantiTect SYBR Green RT-PCR Kit (Qiagen) on an iCycler MyiQ™ Real-Time PCR detection system (Bio-Rad Laboratories, Inc, Hercules, Calif.) according to the manufacturer's instructions. P. gingivalis 16 S rRNA gene was used as a normalizing gene. The melting curve profile was analyzed to verify a single peak for each sample, which indicated primer specificity. The expression levels of the investigated genes for the test sample were determined relative to the untreated calibrator sample by using the comparative cycle threshold (ΔCT) method. ΔCT was calculated by subtracting the average CT value of the test sample from the average CT value of the calibrator sample, and the value used to calculate the ratio between the two by assuming 100% amplification efficiency. By loading the same amount of total RNA for any comparable samples, the ΔCT represents the difference in gene expression between the samples.

body. Visualization was with a LSM 510 inverted confocal microscope with selected filters (543 nm excitation and 560 nm emission).

Pull-down assays. To isolate and identify P. gingivalis surface molecule(s) that interacts with ArcA, we performed a pull-down assay. Surface extracts of P. gingivalis were prepared by sonication with a Sonic Dismembrator (Fisher Scientific; output control 8, 20 s×3), and the cell debris were removed by centrifugation followed by filtration (0.2-μm pore size). Surface extracts of 33277 were mixed with purified ArcA on a rotator at room temperature for 1 h, and then added to an ArcA antibody coupled Sepharose 4B column (Sigma-Aldrich). After incubation at room temperature for 1 h, the column was washed three times with PBS containing 0.01% Tween, and proteins were eluted by 0.1 M Glycine pH 2.4. After SDS-PAGE, bands were excised and identified by liquid chromatography-mass spectrometry.

Construction of the pgn_0294 (ragB) and pgn_0806 (motA/to/Q/exbB) mutants. Insertional mutants (pgn_0294 and pgn_0806) were generated by ligation-independent cloning of PCR mediated mutagenesis (LIC-PCR) 63-65. A 2.1-kb ermF-ermAM cassette was introduced into target genes by three step PCR to yield pgn_0294-erm-pgn_0294 or pgn_0806-erm-pgn_0806 DNA fragments as described previously 64. The final PCR products were then introduced

TABLE 2

Oligonucleotide Primers

| Gene | Primer name | Primer sequences (5'-3') | SEQ ID NO. |
|---|---|---|---|
| fimA | FimA-88F | CGGAACGAATAACCCAGAGA | 15 |
|  | FimA-88R | CTGACCAACGAGAACCCACT | 16 |
| mfa1 | Mfa1-F | CAGATGGGTTGTTGCTCA | 17 |
|  | Mfa1-R | ATGGAAAGTGCTGCTGGTAG | 18 |
| kgp | Kgp-133F | CTATTGGGAACTGCTGTGTTAC | 19 |
|  | Kgp-133R | TCCTCGCCCCAATAAGAATTC | 20 |
| rgp | Rgp-194F | CAACAGCAACCAGCTACCGT | 21 |
|  | Rgp-194R | CGTTCATCTCATCCTGCCCG | 22 |
| rgpA | RgpA-156F | GACGGTTATTAAGACCATCAACAC | 23 |
|  | RgpA-156R | TCCACGCTGCGAGCGGTAT | 24 |
| sod | Sod-235F | AATTCCACCACGGTAAGCAC | 25 |
|  | Sod-235R | GAGCCGAATTGTTTGTCGAT | 26 |
| pgn0128 | Pgn0128-114F | TAATGGGAAGAGCGAGCAGT | 27 |
|  | Pgn0128-114R | ACAGGGCATTTAGCACAACC | 28 |
| 16s-rRNA | 16s-rRNAF | TGGGTTTAAAGGGTGCGTAG | 29 |
|  | 16s-rRNAR | CAATCGGAGTTCCTCGTGAT | 30 |
| arcA | arcA186-F | TCCAATGCCAAACCTTTACT | 31 |
|  | arcA186-R | ATACGAGTATCTTCTTCACG | 32 |

Confocal microscopy. ArcA (50 μg) was purified from S. cristatus CC5A as described (Teles R, Teles F, Frias-Lopez J, Paster B, Haffajee A. 2013. Lessons learned and unlearned in periodontal microbiology. Periodontal 2000 62: 95-162), mixed with P. gingivalis cells ($10^8$) in PBS and incubated at room temperature for 1 h. After washing three times with PBS, bacteria-protein complexes were blocked in PBS with 5% BSA for 1 h. ArcA bound to P. gingivalis was detected by staining with rabbit anti-ArcA polyclonal antibody (1:400) and tetramethyl rhodamine isothiocyanate (TRITC, 1:500)-conjugated AffiniPure Goat Anti-Rabbit IgG antiinto P. gingivalis 33277 by electroporation. Mutants were selected on TSB plates containing erythromycin (5 μg/ml). The insertional mutation was confirmed by PCR analysis, and the mutants were designated as P. gingivalis Δ0806 or ΔragB.

Protein Interaction Screening. Surface extracts of P. gingivalis were collected by sonication (1 min for three times) and centrifugation (13000 g for 30 min) followed by filtration (0.2 μm pore size). Peptide microarray analysis was performed by PEPperPRINT (Heidelberg, Germany). An ArcA microarray was generated with 409 different peptides of ArcA, and each peptide contained 15 amino acids with a peptide-peptide overlap of 14 amino acids. After blocking and washing, the array was incubated with surface extracts (100 μg/ml) isolated from *P. gingivalis* 33277, the 0806 mutant, or the ragB mutant. *P. gingivalis* surface proteins bound on the ArcA array were detected using anti-*P. gingivalis* antibodies and sheep anti-rabbit IgG (H+L) DyLight680. The arrays were analyzed with a LI-COR Odyssey Imaging System.

Peptide synthesis and activity. Peptides were synthesized by PEPperPRINT and Biomatik (Delaware) and purified with High Performance Liquid Chromatography (HPLC) at 90% purity. Peptides were resuspended in nuclease/proteinase-free PBS, aliquoted, and stored at −20° C. Inhibitory activity of peptides were determined as described (Hajishengallis, G., Darveau, R. P. & Curtis, M. A. The keystone-pathogen hypothesis. *Nature reviews. Microbiology* 10, 717-725, doi:10.1038/nrmicro2873 (2012)) with slight modification. Peptides were mixed with $5\times10^5$ cells of *P. gingivalis*, spotted onto a TSB blood agar plate, and cultured for 60 h anaerobically. The expression levels of fimbrial and gingipain mRNA or proteins were measured using qRT-PCR or western blot analyses.

Western Blot Analysis. *P. gingivalis* cells were lysed using BUGBUSTER® Protein Extraction Reagent (EMD Millipore, Darmstadt, Germany), and the protein concentration determined using a Bio-Rad protein assay (Bio-Rad). Lysates (0.5 μg) were separated by 12% sodium SDS-PAGE, and transferred to nitrocellulose membranes (Invitrogen, Carlsbad, Calif.) with a Mini Transblot Electrophoretic transfer cell (Bio-Rad) at 100 V for 1 h. The membrane was blocked with 3% BSA in PBS for 1 h and incubated with polyclonal anti-FimA, anti-Mfa1, anti-HGP44 (a C-terminal adhesin domain of gingipains), or anti-PGN-0128 antibodies diluted 1:1,000 for 1 h. After washing with PBS, the membrane was incubated with anti-rabbit horseradish peroxidase-conjugated secondary antibodies for 1 h. The proteins were visualized using enhanced chemiluminescence (GE Healthcare Bio-Sciences Corp, Pittsburgh, Pa.) and measured using a semi-quantitative Western blot technique with ImageJ software (NIH, Bethesda, Md.).

Transmission electron microscopy. *P. gingivalis* cells were grown on TSB blood plates for 48 h with or without peptide4. Bacterial cells were collected and resuspended in PBS. 20 μl of bacterial suspension were applied to a Formvar-coated copper grid (200 mesh, Electron Microscopy Sciences, PA) and air dried. The bacterial cells were then negatively stained with 0.5% ammonium molybdate for 4 min and observed with a transmission electron microscope (Philips CM-12, Portland, Oreg.) operated at 80 kV.

Statistical analyses. A student's t-test was used to determine the statistical significance of differences in gene expression profiles and growth rates of *P. gingivalis* strains. A p<0.05 was considered significant.

Results

Figure 1A:
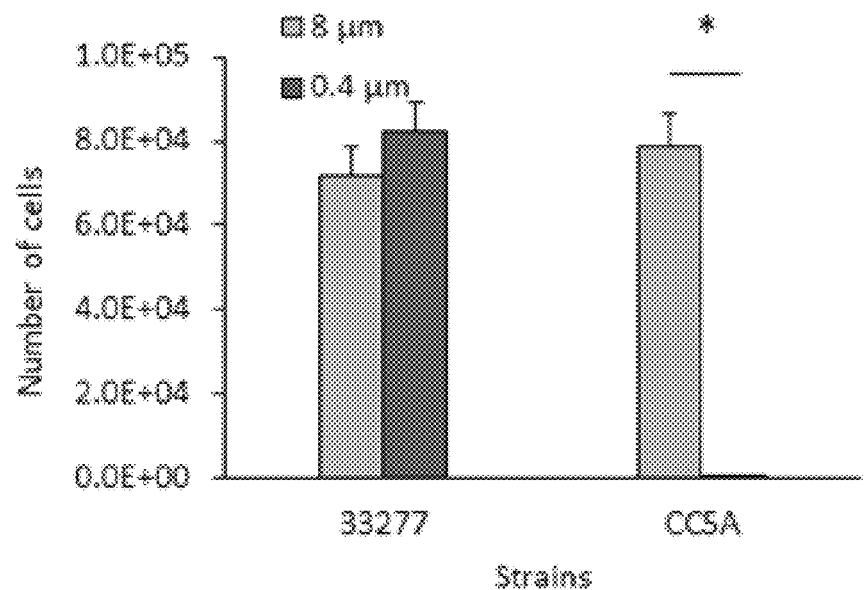
FIGS. 1A-1B show the expression of fimA in *P. gingivalis* in contact with *S. cristatus*. Error bars represent standard deviations. An asterisk indicates a statistically significant difference in expression level of fimA in *P. gingivalis* (n=3; t test; p<0.05).
Figure 1B:
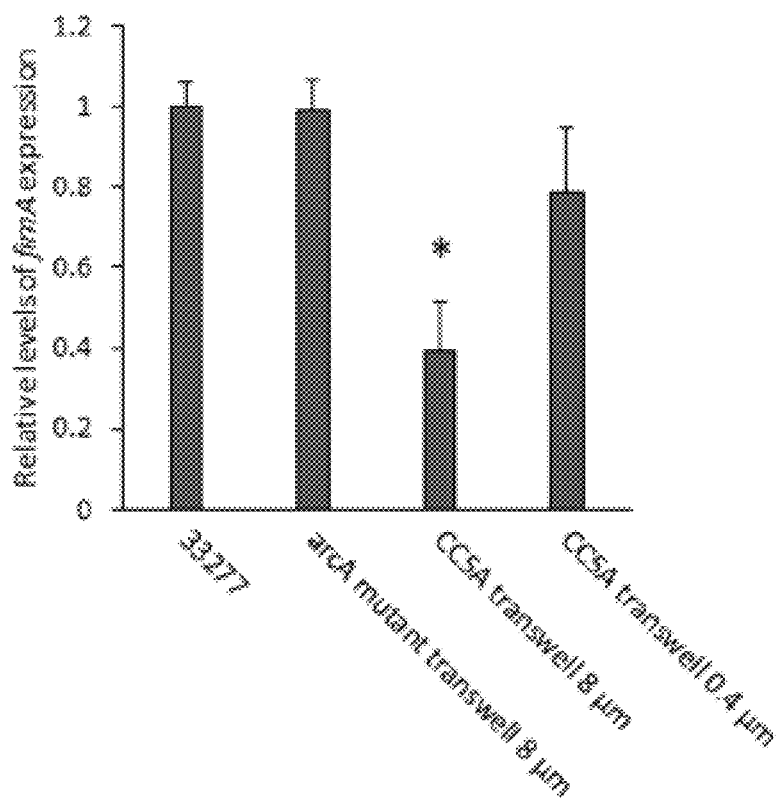

Direct contact is required for *P. gingivalis-S. cristatus* communication. To test if *P. gingivalis-S. cristatus* communication occurs through direct cell-cell contact, *P. gingivalis* 33277 and *S. cristatus* CC5A or its arcA mutant were separated using a transwell system with a membrane of pore size either 0.4 μm or 8 μm. After 16 h, bacteria in each the lower well were collected, and numbers of *P. gingivalis* 33277 and *S. cristatus* CC5A were determined using qPCR. $7.8\times10^4$ from an input of $1\times10^7$ CC5A cells migrated to the lower well from the Transwell insert through 8 μm pores, whereas less than 1.5 *S. cristatus* cells were detected in the lower well when using the membrane with 0.4 μm pore (FIG. 1A). *P. gingivalis* RNA was then purified and expression of the fimA gene measured using qRT-PCR. Levels of fimA expression were reduced about 2.5 fold when the 8-μm pore transwell was used (FIG. 1B). Inhibition of fimA expression by *S. cristatus* was not observed when *P. gingivalis-S. cristatus* contact was blocked by the 0.4 μm pore membrane, suggesting that direct contact is required for cell-cell communication between *P. gingivalis* and *S. cristatus*.

Figure 2:
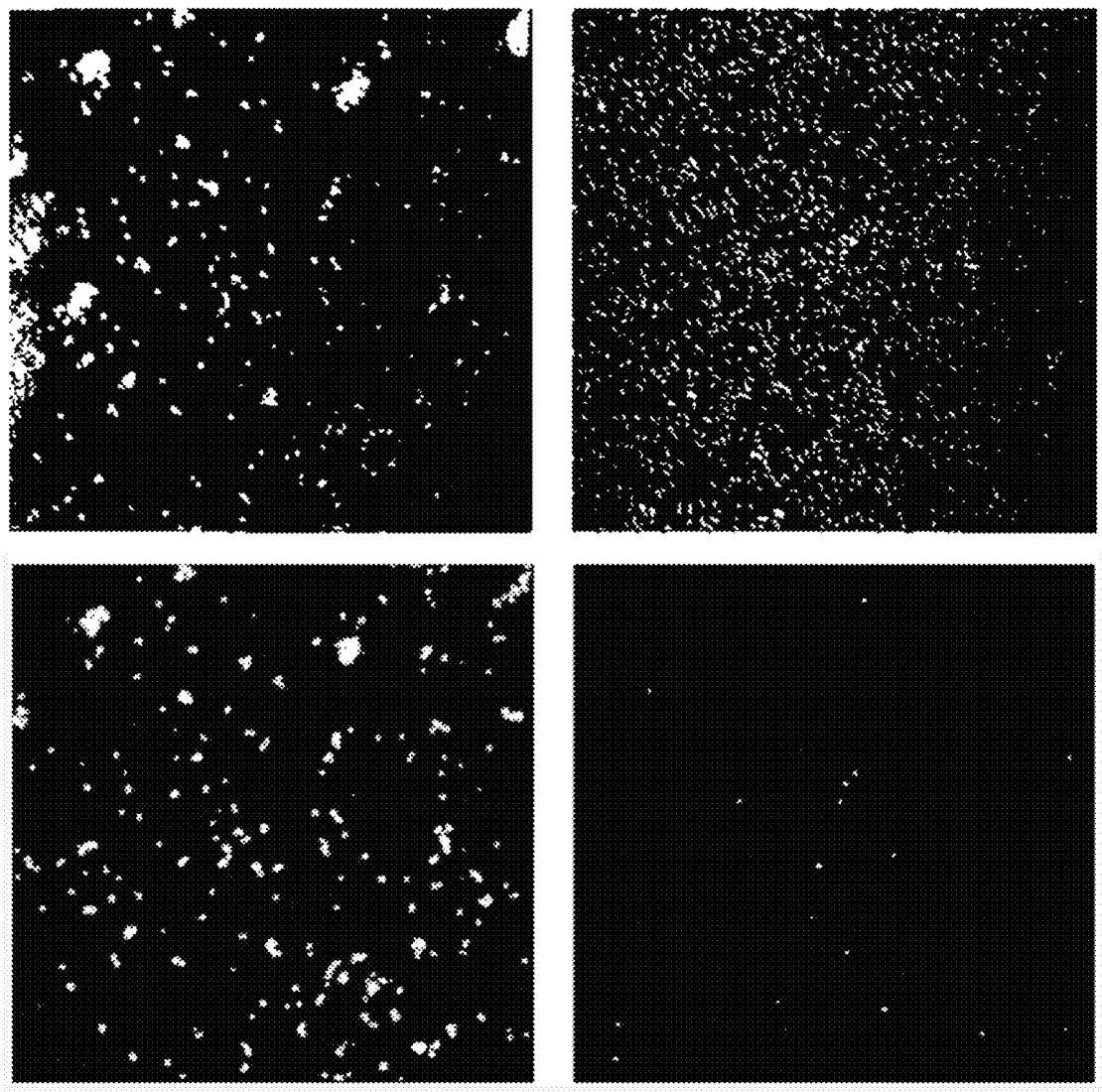
FIG. 2 shows immunofluorescence antibody images of interaction of *P. gingivalis* 33277 or *A. actinomycetemcomitans* Y4 and ArcA. The upper panel presents differential interference contrast (DIC) images showing the location of the bacteria. The red images in the lower panel are the TRITC fluorescence labeling images representing *S. cristatus* ArcA bound to *P. gingivalis* 33277 or *A. actinomycetemcomitans* Y4 that are positively labeled by ArcA specific antibody.

Direct interaction of *P. gingivalis* and *S. cristatus* ArcA was confirmed by an immunofluorescence assay with *P. gingivalis* cells and purified ArcA protein. Fluorescent labeled *P. gingivalis*-ArcA complexes were detected by confocal microscopy. As shown in FIG. 2, ArcA had high affinity for *P. gingivalis* 33277, but not for AaY4, suggesting a specific interaction between ArcA and *P. gingivalis* surface molecules.

Figure 3:
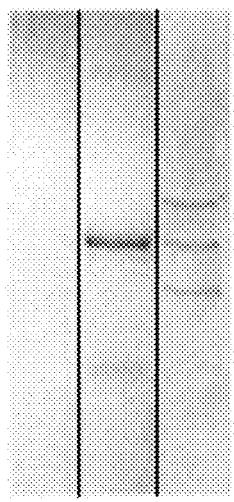
FIG. 3 shows the interaction of ArcA and *P. gingivalis* surface proteins. SDS-PAGE analysis shows that three major bands were detected as *P. gingivalis* RagB (PGN_0294) protein, *S. cristatus* ArcA, and a MotA/ToIQ/ExbB proton channel family protein (PGN_0806): Lane 1, *P. gingivalis* extract only; Lane 2, CC5A extract only; and Lane 3, *P. gingivalis* and *S. cristatus* CC5A extracts.

Isolation of *P. gingivalis* surface protein(s) that interacts with ArcA of *S. cristatus*. To isolate and identify *P. gingivalis* surface molecule(s) that interact with ArcA, a pull-down assay was performed. An ArcA antibody coupled Sepharose 4B column was used to capture ArcA-interacting components from a mixture of *P. gingivalis* cell lysate and ArcA protein. The proteins eluted from the column were analyzed with SDS-PAGE. Three bands with molecular sizes of approximately 55, 47, and 30 kDa were detected (FIG. 3). Western blot using ArcA antibody showed that the 47 kDa protein is ArcA of *S. cristatus* (data not shown). The other two bands were identified by MS analysis as *P. gingivalis* RagB (PGN_0294) and a MotA/TolQ/ExbB proton channel family protein (PGN_0806), suggesting that these two proteins are receptors for ArcA.

Figure 4:
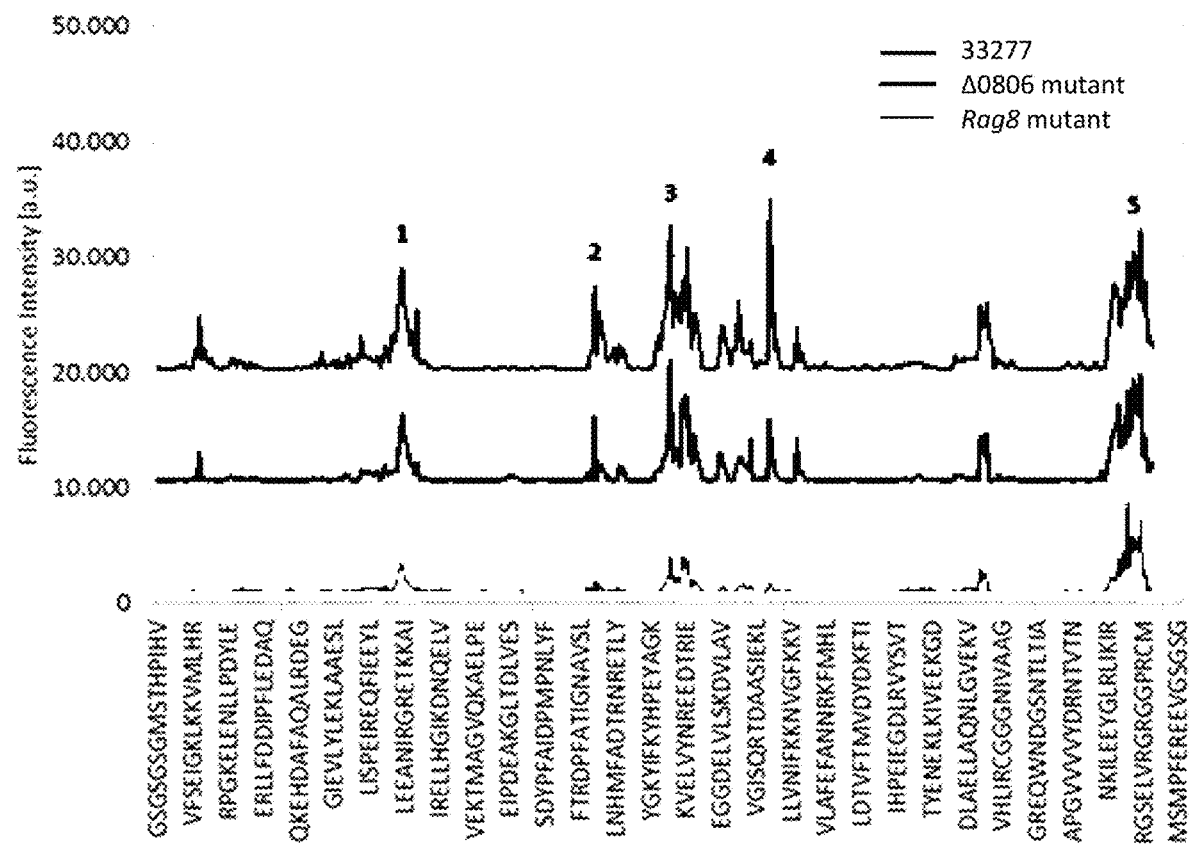
FIG. 4 shows the relative binding of an assortment of peptides with surface extracts of *P. gingivalis* 33277 (top trace), the 0782 mutant (middle trace), and the ragB mutant (bottom trace). The intensity plot of peptide array signals shows as peaks with corresponding regions of ArcA. The five highest peaks are numbered.

Identification of the key functional motif of ArcA. *S. cristatus* ArcA is a 47 kDa protein with 409 amino acids. We sought to identify key amino acids and the motif(s) of ArcA responsible for its inhibitory activity toward fimA expression. A peptide microarray was first performed to detect binding sites of ArcA for *P. gingivalis*. The arrays were incubated with surface extracts of *P. gingivalis* 33277, or the ΔragB or Δ0806 mutants, and binding was detected with *P. gingivalis* antibodies. Although the absolute binding capacities (fluorescence intensity) of these strains were significantly varied, likely due to protein degradation of surface extract in some strains, the overall patterns were consistent. Of several peaks observed (FIG. 4), a peptide with SEQ ID NO: 6 having the sequence NIFKKNVGFKK (peak 4) and spanning amino acid residues 249-259, was found to have the highest binding affinity to *P. gingivalis* 33277 proteins, evident as the highest peak. This peak was no longer the highest when the arrays were incubated with surface extracts isolated from the Δ0806 or ΔragB mutants, corroborating the involvement of *P. gingivalis* proteins PGN_0806 and RagB in recognition of ArcA.

Figure 5:
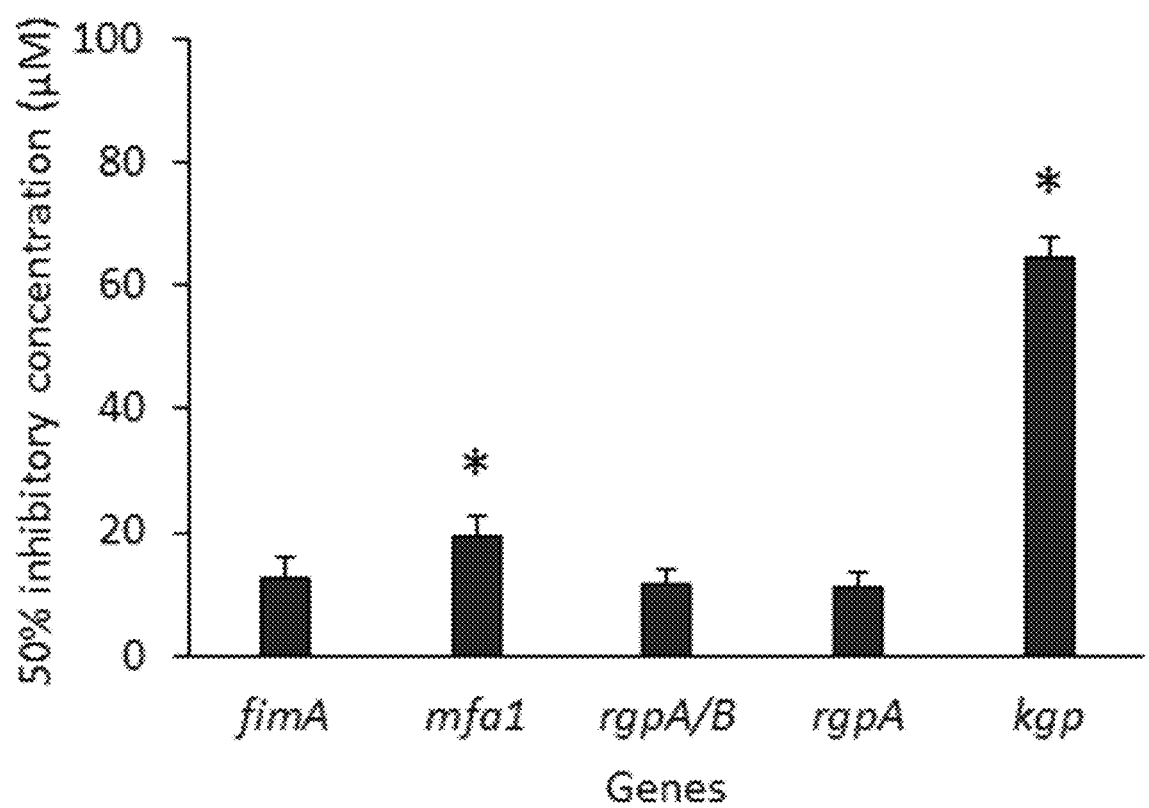
FIG. 5 shows the potency of peptide4 for inhibition of virulence gene expression in *P. gingivalis*. The half inhibitory concentration (IC50) was measured by conducting three independent experiments to determine mRNA levels of fimA, mfa1, rgpA/B, and kgp in the presence of peptide4 at the concentrations 0, 4, 16, and 64 µM, respectively. The IC50 for each gene was established using a Microsoft Excel program with add-in for curve fitting. Asterisks indicate the statistical significances of IC50 of peptide4 for a specific gene when compared to that for the fimA gene (P<0.05; t test).

Five peptides (1-5 in TABLE 1) were synthesized based on ArcA array peaks, and the effect of each peptide on gene expression was determined by inclusion of the peptides in the *P. gingivalis* growth media. As shown in TABLE 3, the 11 residue peptide4 from the C-terminal region of ArcA repressed expression of fimA, mfa1, kgp, rgpA/B (encoding catalytic regions of rgpA/B), and rgpA (encoding adhesin domains of RgpA) genes by at least 2 fold, at a concentration of 16 μM. Expression of pgn_0128 encoding immunoreactive 53 kDa antigen was not modulated in response to the presence of peptide4, indicating specificity for a subset of virulence-associated genes. Increased inhibitory activity (60-70%) was observed at a concentration of 64 μM (not shown), suggesting that this region is likely a key active motif of ArcA. These results also establish that the effects of ArcA on *P. gingivalis* virulence extend beyond repression of fimA and include genes for the gingipains and for the minor fimbrial subunit, as also shown by others. The half inhibitory concentration (IC50) was determined by constructing a dose-response curve (0, 4, 16, and 64 µM) to measure the effectiveness of peptide4 in repressing expression of these genes. As shown in FIG. 5, the highest efficiency of peptide4 was found in inhibition of rgpA (amplified with primers corresponding to the region encoding the binding domain of RgpA, HGP44), rgpA/B (amplified with primers corresponding to the region encoding catalytic regions of RgpA and B), and fimA with IC50s of 11.2±2.1, 11.7±2.3 or µM, 12.4±3.4, respectively. Peptide4 also showed a significantly lower IC50 for mfa1 (19.2±3.3 µM) compared to that of kgp (64.3±3.8 µM). It should be pointed out that peptide1, 2, 3 and 5 (TABLE 3) also exhibited some inhibitory activity, although at a lower efficiency. These regions along with peptide4 may be involved in formation of a structural motif that may have a higher binding capacity than peptide4 alone. These findings provide a molecular basis for the future design of inhibitors of *P. gingivalis*.

mately 20 and 4 fold in the fimS and fimR mutants (data not shown), Peptide4 mediated regulation of FimA expression reminded intact in the absence of FimS and FimR (FIG. 6B), suggesting FimS/R is not involved in this bacterial cell-cell communication. These results provide strong evidence that PGN_0806 and RagB, either separately or in combination, act as receptors in the bacterial cell-cell communication between *P. gingivalis* and *S. cristatus*.

Figure 7A:
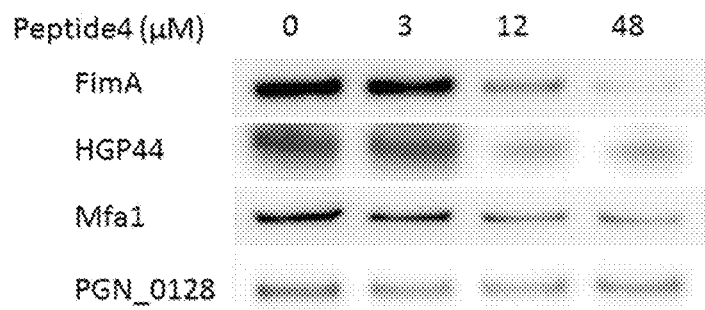
FIGS. 7A-7B show the production of fimbrial proteins and gingipains in *P. gingivalis* in response to peptide4. (A) Expression levels of FimA, Mfa1, Hgp44 of gingipains, and PGN_0128 (immunoreactive 53 kDa antigen) in surface extracts of *P. gingivalis* 33277 exposed to pwptide4 at concentrations 0, 3, 12, and 48 µM were analyzed using a Western blot analysis. (B) Semiquantitation of western blots was conducted with ImageJ software. Each bar represents the intensity of the protein band. An asterisk indicates a significant difference between the relative intensity of the protein bands in *P. gingivalis* exposed to peptide4 (3, 12, or 48 µM) compared to those seen in *P. gingivalis* not exposed (0 µM, 1 unit) (P<0.05 by t test).
Figure 7B:
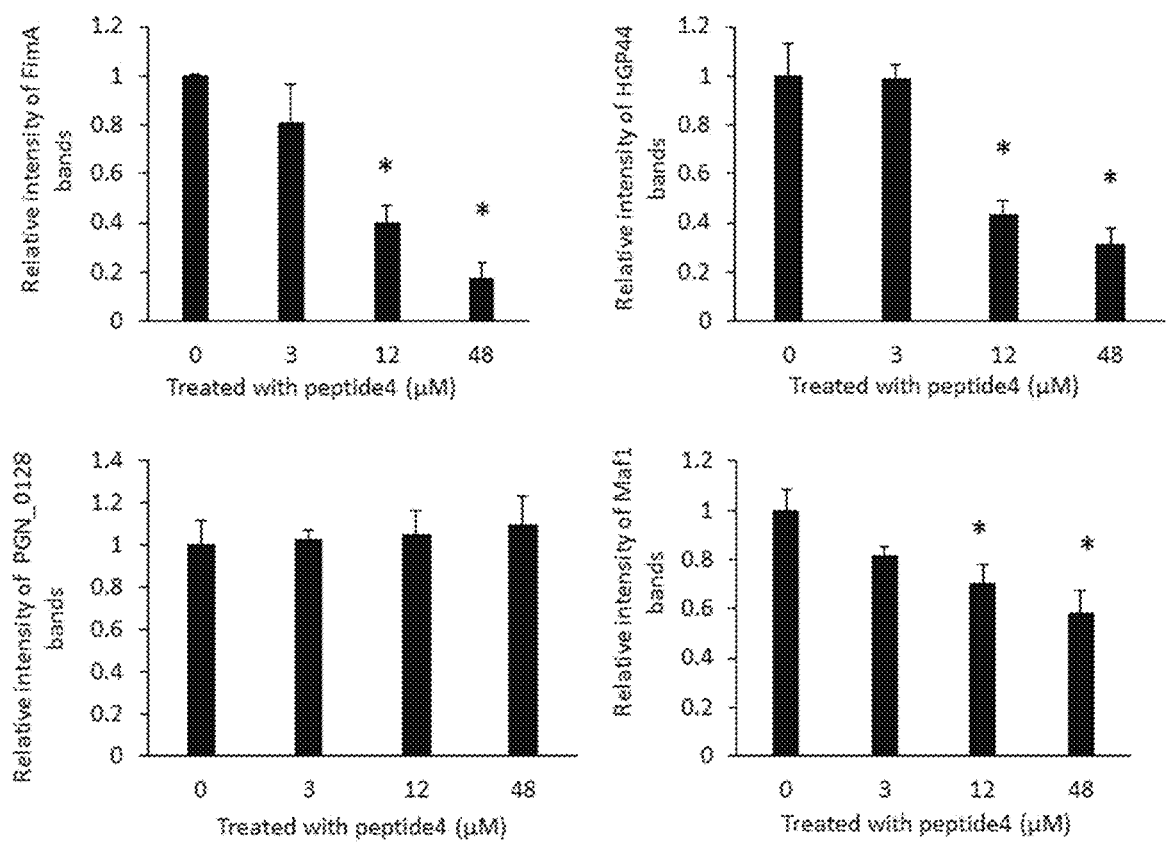
Figure 8A:
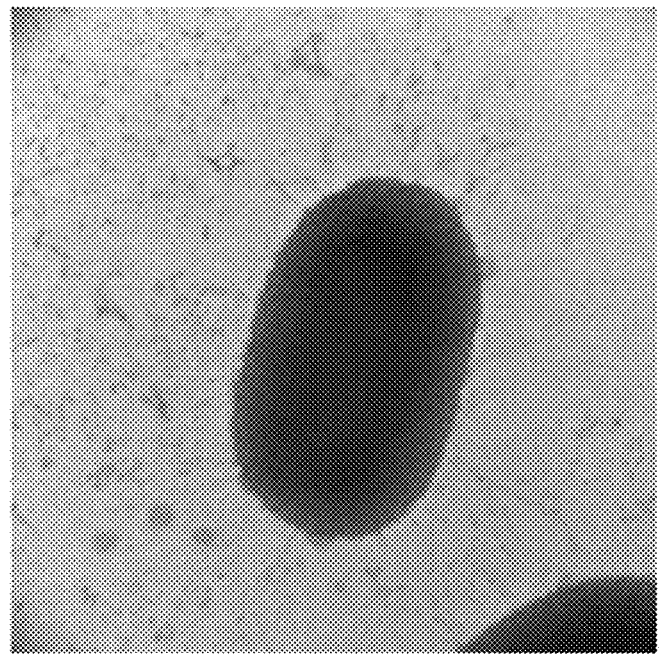
FIGS. 8A-8B show the transmission electron microscopic analysis of *P. gingivalis* fimbriae. Fimbrial structures were visualized using TEM. *P. gingivalis* strains 33277 (A) and 33277 treated with peptide4 (B) were grown on the TSB plate for 48 h and prepared by negatively staining with ammonium molybdate. Bars=0.2 µm.
Figure 8B:
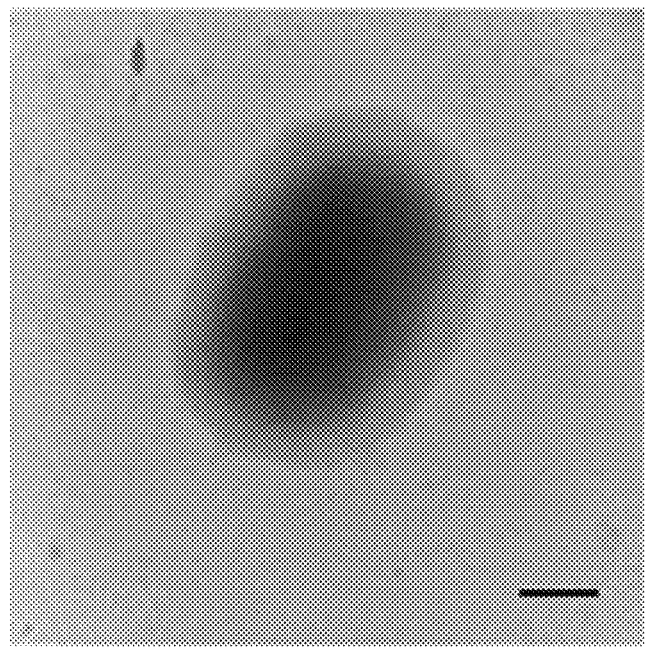

Expression of fimbrial proteins and gingipains at the translational level was also determined using Western blot analysis. *P. gingivalis* 33277 was grown with peptide4 at concentrations of 0, 3, 12, and 48 µM (0×, ¼×, 1×, and 4× IC50 of fimA expression) for 48 h. As shown in FIGS. 7A and 7B, production of FimA, Mfa1, and HGP44 (a binding domain of RgpA) was significantly decreased in the presence of 12 and 48 µM of peptide4. However, production of immunoreactive 53 kDa antigen was not altered, consistent with the expression pattern observed at the transcriptional level. Transmission electron microscopy further showed that there were few fimbriae on the surface of *P. gingivalis* grown in media supplemented with peptide4 (16 µM), when compared to *P. gingivalis* cells grown without peptide4 (FIGS. 8A and 8B).

TABLE 3

| Peptide | Peptide sequence and residue position | Relative expression level | | | | | |
|---|---|---|---|---|---|---|---|
| | | fmA | mfa1 | rgpA/B | rgpA | kgp | pgn0128 |
| P1 | $I_{97}$RGRETKK | 0.88 ± 0.88 | 0.85 ± 0.05 | 0.89 ± 0.05 | 0.86 ± 0.07 | 1.06 ± 0.12 | 0.96 ± 0.06 |
| P2 | $N_{177}$HMFADTRNRE | 0.80 ± 0.03 | 0.80 ± 0.10 | 0.78 ± 0.07 | 0.81 ± 0.03 | 0.90 ± 0.05 | 0.88 ± 0.03 |
| P3 | $V_{208}$YNREEDTRIEGGDEL | 0.87 ± 0.10 | 0.82 ± 0.07 | 0.98 ± 0.06 | 0.84 ± 0.06 | 0.99 ± 0.12 | 0.91 ± 0.07 |
| P4 | $N_{249}$IFKKNVGFKK | 0.40 ± 0.06* | 0.51 ± 0.05* | 0.38 ± 0.04* | 0.39 ± 0.04* | 0.47 ± 0.06* | 0.94 ± 0.06 |
| P5 | $E_{389}$LVRGRGGPRCMSMPF | 0.97 ± 0.05 | 0.83 ± 0.04 | 0.72 ± 0.05 | 0.73 ± 0.06 | 0.96 ± 0.12 | 0.91 ± 0.06 |

The above TABLE 3 shows differential expression of virulence genes in *P. gingivalis* in the presence of ArcA peptides. *P. gingivalis* 33277 was grown TSB in the presence or absence of peptide at a concentration 16 µM. Transcript levels were measured by real-time PCR. The mRNA levels of genes are indicated relative to the expression level in the absence of peptides as 1 unit. Results shown are means and standard deviations from three independent experiments. Asterisks indicate the statistical significance of expression levels at least two fold in *P. gingivalis* grown in TSB with/without peptides ($P<0.05$; t test).

Figure 6A:
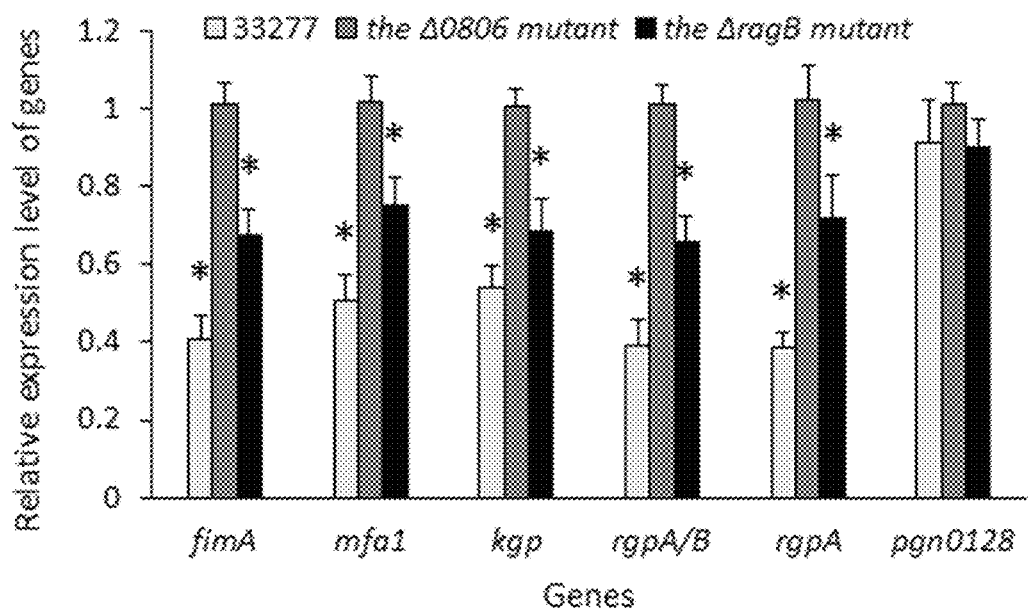
FIGS. 6A-6B show the comparison of virulence gene expression in *P. gingivalis* 33277 and its mutants. Expression of fimA, mfa1, rgpA/B, rgpA, and kgp was determined using qRT-PCR. *P. gingivalis* strains were grown TSB in the presence or absence of peptide4 at a concentration 16 µM. (A) The mRNA levels of genes in 33277, the pgn_0806, and the ragB mutants grown in the media supplemented with peptide4 are indicated relative to the expression level in *P. gingivalis* 33277 grown in the medium without peptide4 (1 unit). (B) The fimR (ΔfimR) and fimS (ΔfimS) mutants were grown with or without the peptide4. Each bar represents relative expression level of fimA or mfa1 in the mutants grown with peptide4 (16 µM) to those in the mutant grown in the media without peptide4 (1 unit). Results shown are means and standard deviations from three independent experiments. Asterisks indicate the statistical significance of expression levels of genes in *P. gingivalis* strains grown with/without peptides (P<0.05; t test).

To verify that PGN_0806 and RagB function as receptors in *P. gingivalis-S. cristatus* communication, gene expression in the Δ0806 and ΔragB strains in the presence or absence of peptide4 and compared these to that in the wild type strain 33277 were tested. The results showed that loss of PGN_0806 prevented peptide4-dependent regulation of fimA, mfa1, rgp, and kgp (FIG. 6A). Although the ragB mutation did not completely block peptide4 activity, a significantly reduced inhibitory effect was observed toward all of the target genes. Previously, a two component regulatory system (FimS/R) was identified to be activator of fimA expression. The role of FimS/R in *S. cristatus-P. gingivalis* cell-cell communication was tested. Although expression levels of fimA and mfa1 were repressed approxi- Discussion Five ArcA binding regions have been discovered. Of note is a functional motif of ArcA, located at the C-terminal and spanning amino acids 249-259, and a peptide (peptide4) derived from this region showed inhibitory activity for both mRNA and protein expression of fimbriae (FimA and Mfa1) and gingipains (RgpA/B and Kgp). Hence this peptide is a potential candidate for developing inhibitors against *P. gingivalis*. Based on our observation that ArcA specifically binds to the surface of *P. gingivalis*, it is likely that the peptide inhibitors would be specific for this organism and not have a significant inhibitory effect on early biofilm colonizers (streptococci and actinomyces). Targeting *P. gingivalis* alone would likely be sufficient to impede the development of a dysbiotic biofilm, as *P. gingivalis* is considered a keystone pathogen.

Cell surface receptors are important elements in signal transduction, and possess the ability to bind (sense) a specific signal, subsequently eliciting a specific cellular response. A well-known signal transduction process in bacteria involves two-component regulatory systems which involve a sensor histidine kinase and a response regulator protein. The FimS/R two-component signal transduction in *P. gingivalis* predominantly regulates fimA expression and some other genes including mfa122. However, results from the current study showed that FimS/R was not involved in communication between *P. gingivalis* and *S. cristatus*, since expression levels of fimA and mfa1 in the fimS or fimR mutants were also modulated in response to peptide4. However, two *P. gingivalis* surface proteins, RagB (PGN_0294), a major immunodominant antigen of *P. gingivalis*, and PGN_0806 annotated as a MotA/ToIQ/ExbB proton channel family protein, which interact with ArcA of *S. cristatus*, especially with the peptide4 region of ArcA were identified. Interestingly, the *Pseudomonas aeruginosa* TonB-ExbB-ExbD protein complex is reported to be involved in signal transduction. Moreover, RagA, which is thought to associate with RagB on the *P. gingivalis* surface, is a TonB-dependent receptor. This work demonstrates that mutation in the ragB gene partially blocks the inhibitory activity of ArcA against fimA, while the *P. gingivalis* strain carrying mutation in the pgn_0806 gene was completely abrogated in response to peptide4. These data corroborate the role of PGN_0806 and RagB, as receptors, in *P. gingivalis-S. cristatus* communication. Although a signal peptide and potential receptor(s) were identified, the mechanisms of intracellular signal transduction are still unidentified. A previous study showed that expression of rgpA, but not kgp, was decreased in a prtT mutant, which indicated that expression of kgp and rgp is not coordinately regulated. Therefore, it is speculated that independent intracellular transmitters are involved in control of fimA, mfa1, kgp, and rgp.

In conclusion, a functional domain of *S. cristatus* ArcA was identified that has high affinity to the surface of *P. gingivalis* and is able to repress expression of several well-known virulence genes involved in production of fimbriae and gingipains. Two surface proteins of *P. gingivalis*, RagB and PGN_0806 were uncovered, which interact with ArcA and are required for bacterial cell-cell communication between *P. gingivalis* and *S. cristatus*. These results functionally characterize and molecularly dissect the antagonistic relationship between these oral bacteria that we reported earlier. Application of these findings should provide the basis for therapeutic strategies designed to reduce colonization of *P. gingivalis* in the oral cavity and suppress the pathogenicity of periodontitis-associated dental plaque.

Prophetic Example 2

Characterization and Design of Small Peptides Derived from Functional Domains of ArcA that Repress Expression of FimA and Gingipain Genes in *P. gingivalis*

ArcA is a major cell wall associated surface protein of group A streptococci. ArcA acts as an efficient inhibitor of fimA expression and biofilm formation of *P. gingivalis*. The objective of this prophetic example is to design a more potent inhibitor that can repress expression of virulence gene expression in *P. gingivalis* and to optimize properties of the peptide inhibitor. It is hypothesized that a short peptide derived from ArcA is likely sufficient in the regulation of virulence gene expression in *P. gingivalis*. Therefore this section focuses on the mechanism involving the direct role of ArcA on *P. gingivalis* virulence potential. In vitro functional studies including enzymatic, gene expression and colonization assays will be performed to confirm this model. *P. gingivalis* strains including both fimbriated strain 33277 and afimbriated strain W83 will be tested and compared for their responses to the peptide inhibitors.

The preliminary data showed that P4 repressed expression of fimA and rgp genes by approximately 50%, at a concentration of 15 µM. To generate a functional peptide with higher inhibitory activity, longer peptides will be created to facilitate formation of the secondary structures and to restore the three-dimensional structure of ArcA functional motif. Secondary structure prediction of ArcA using softwares Jpred4, Psipre, and Jufo9D suggests that P4 seems at the end of an alpha helix, which is followed by a few random coil residues, and the beginning of a beta sheet after that. Therefore, 19 mer- and 27 mer-peptides will be designed by adding 4 or 8 residues at each end of P4, respectively, based on the sequence of ArcA. The ability of the peptides to repress expression of fimA and rgp will be tested and compared. If an increased inhibitory activity is found in the longer peptides compared to P4, the peptide with the highest activity will be further analyzed by creating two peptides with additional residues at only one end of P4. For example, if P4 with additional residues at the N-terminal end shows a higher inhibitory activity, an alpha helix is likely critical for the functional activity.

Once the length of P4 is determined, key residues will be determined using a mutagenesis approach, such as an Alanine screen. The residues in P4 will be systematically substituted by alanine, which eliminates side-chain interactions without altering main-chain conformation. A peptide library will then be constructed, which will have a systematic combination of amino acids at the key residues.

Peptide cyclisation will also be employed to enhance inhibitory activity of the functional peptide. Cyclic peptides may provide specific conformational properties by modifying the interaction of the side chains.

These peptide analogs will be tested, despite their inhibitory activity, for their solubility, stability, and cytotoxicity. P4 can be dissolved in buffer (PBS) and TBS (growth medium of *P. gingivalis*), however, modification of the peptide may impact solubility of its analogs. If it is the case, non-essential hydrophobic amino acids will be substituted with charged or polar residues. To test stability of peptide inhibitors, the peptides will be mixed incubated 1) at 37° C.; 2) in saliva; and 3) in the presence of *P. gingivalis* cells for 24 h. MS spectra will be acquired in positive mode with data dependent MS/MS scan fragmenting the most abundant peak from the preceding scan. The initial study showed that P4 is stable at 37° C. for 24 h. If degradation is rapidly detected, non-essential amino acids of the active peptide will be replaced with non-natural amino acids. Non-proteinogenic amino acids may improve peptide stability. Biological effects of the peptides on oral cells will be examined. Human oral keratinocytes (HOK) and gingival fibroblasts (HGF) (ScienCell Research Laboratories) will be exposed to 60 or 15 µM peptides for 24 or 48 h. Lactate Dehydrogenase (LDH) assay will be performed by assessing LDH released into the media as a marker of dead cells or performing lysis LDH as a marker of remaining live cells.

The ultimate goal is to identify a potent peptide inhibitor that will be selected by functional assays including determination of mRNA levels of virulence genes, gingipain activity, fimbrial formation, and biofilm formation of *P. gingivalis*. Inhibitory effects of the peptides on virulence gene expression in *P. gingivalis* will be measured using RT-qPCR as described (Wang B Y, Wu J, Lamont R J, Lin X, Xie H. 2009. Negative correlation of distributions of *Streptococcus cristatus* and *Porphyromonas gingivalis* in subgingival plaque. *J Clin Microbiol* 47: 3902-6). Expression of virulence genes involved in fimbrial formation (fimA), proteinase activity (rgpA, and rgpB), and iron acquisition systems (hmuX and Y) will serve as a selected marker for peptide inhibitors. The half maximal inhibitory concentration (IC50) determined by constructing a dose-response curve will be a measure of the effectiveness of a peptide in repressing expression of these genes and a standard for functional assays. All functional assays will be performed using a series diluted dose including 4×C50, IC50, and ¼×IC50.

In the event that a potent peptide inhibitor is identified, fimbriae displaying on the surface will be examined using a transmission electron microscopy after treatment of *P. gingivalis* with peptide inhibitor (Kadowaki, T. et al. Arg-gingipain acts as a major processing enzyme for various cell surface proteins in *Porphyromonas gingivalis*. *The Journal of biological chemistry* 273, 29072-29076 (1998)). The effect of peptide inhibitors on the formation of *P. gingivalis* and *P. gingivalis-Streptococcus gordonii* heterotypic biofilms will be examined as described (Eke, P. I. et al. Update on Prevalence of Periodontitis in Adults in the United States: NHANES 2009 to 2012. *Journal of periodontology* 86, 611-622, doi:10.1902/jop.2015.140520 (2015); Capestany C A, Kuboniwa M, Jung I Y, Park Y, Tribble G D, Lamont R J. 2006. Role of the *Porphyromonas gingivalis* InlJ protein in homotypic and heterotypic biofilm development. *Infect Immun* 74: 3002-5). Bacterial biofilms will be generated on six-well plates and quantified using qPCR or on glass-bottom dishes and analyzed using confocal microscopy. The role of peptide inhibitor in inhibition of *P. gingivalis* invasion will also be investigated using confocal and antibiotic protection assay (Ho M H, Chen C H, Goodwin J S, Wang B Y, Xie H. 2015. Functional Advantages of *Porphyromonas gingivalis* Vesicles. PLoS One 10: e0123448; Chaudhuri S, Pratap S, Paromov V, Li Z, Mantri C K, Xie H. 2014. Identification of a diguanylate cyclase and its role in *Porphyromonas gingivalis* virulence. *Infect Immun* 82: 2728-35). To further test the role of the peptide inhibitor, an ex-vivo experiment will be conducted using dental plaque samples collected from periodontitis patients. The subject population will consist of 40 male and female between 21 and 65 years of age. The subjects will be recruited from the Dept. of Periodontology at Meharry Medical College. Based on the definition of American Academy of Periodontology (Wilensky, A., Polak, D., Houri-Haddad, Y. & Shapira, L. The role of RgpA in the pathogenicity of *Porphyromonas gingivalis* in the murine periodontitis model. *Journal of clinical periodontology* 40, 924-932, doi:10.1111/jcpe.12139 (2013)), periodontitis subjects should have >16 teeth, 2 or more interproximal sites with CAL >4 mm and 2 or more with pocket depth >5 mm. The criteria of inclusion will have no periodontal treatments in the previous one year for scaling and root planing, or in the previous five years for periodontal surgeries. All subjects will be consented prior to initiation of the study. Supragingival and subgingival plaque samples will be taken from enrolled subjects before any dental treatment, using sterile paper points from the mesio-buccal sulci of a first molar, a first premolar, a canine and a central incisor as described (Wang B Y et al., supra). Paper points will be placed in the sulci for 30 sec and will be transferred in 5 ml TSB in test tubes. The tubes will then immediately be placed in an anaroebical chamber, the bacteria will be cultured for 24 h. Each sample will then be subcultured in two wells (2.5 ml each) in a 6 well plate with/without the peptide inhibitor and continued to be cultured for 48 h to form mixed-species biofilms. Planktonic (free floating) or sessile (anchored) bacteria will be collected and resuspended in Trizol. *P. gingivalis* will be enumerated with qPCR using a QuantiTect SYBR Green PCR Kit with *P. gingivalis* species-specific 16S rRNA gene primers. Standards used to determine the number of *P. gingivalis* will be prepared using genomic DNAs from the wild type strain 33277. Once *P. gingivalis* is detected, the fimA genotype of the strains will be determined using PCR analysis with fimA genotype specific primers as probes (Zheng C, Wu J, Xie H. 2011. Differential expression and adherence of *Porphyromonas gingivalis* FimA genotypes. Mol Oral Microbiol 26: 388-95).

The Arg- and Lys-specific enzymatic activities of *P. gingivalis* grown in the presence of peptide inhibitors will be determined using fluorogenic substrates, L-arginine-7-amino-4-methylcoumarin (L-Arg-AMC) and L-lysine-7-amino-4-methylcoumarin (L-Lys-AMC), respectively (Olsen, I. & Potempa, J. Strategies for the inhibition of gingipains for the potential treatment of periodontitis and associated systemic diseases. *Journal of oral microbiology* 6, doi:10.3402/jom.v6.24800 (2014)) and compared to those of *P. gingivalis* without exposure of peptide inhibitors.

The proposed peptide design will lead to a more potent peptide inhibitor with effectiveness of IC50≤1 μM in repressing expression of virulence genes such as fimA and rgp. It is anticipated that, like the P4, a potent peptide inhibitor will repress expression of several well-known virulence gene expression including genes encoding adhesins and proteinases. As the results production and formation of fimbriae of *P. gingivalis* will be reduced or abnormal, and binding activity of *P. gingivalis* is likely significantly decreased in the presence of a peptide inhibitor. However, if a more potent peptide than P4 cannot be identified, an alternative strategy is to search for an efficient combination of two or more stort peptides to enhance the inhibitory activity. We will design peptides based on the natural amino acid sequences of other binding peaks, since we have found that other peptides also exhibited some inhibitory activity, although at much higher concentrations.

Working Example 3

Effect on Phenotypic Virulence Properties of *P. gingivalis*

Examples above demonstrate that an 11-mer peptide (P4) derived from *Streptococcus cristatus* arginine deiminase (ArcA) was able to repress the expression and production of several well-known *P. gingivalis* virulence factors including fimbrial proteins and gingipains. This work was expanded to ascertain the impact of this peptide on phenotypic properties of *P. gingivalis* related to virulence potential. It was found that while growth rate was not altered by exposure of *P. gingivalis* to P4, monospecies and heterotypic biofilm formation and invasion of oral epithelial cells were inhibited. Additionally, P4 was able to impinge the ability of *P. gingivalis* to dysregulate innate immunity by repressing gingipain-associated degradation of 1L8. Hence, P4 has characteristic that could be exploited for the manipulation of *P. gingivalis* levels in oral communities and preventing realization of virulence potential.

Methods

Bacterial strains and growth conditions. *P. gingivalis* strains were cultured from frozen stocks in either Trypticase soy broth (TSB) or on TSB blood agar plates supplemented with yeast extract (1 mg/ml), hemin (5 μg/ml), and menadione (1 μg/ml), and incubated at 37° C. in an anaerobic chamber (85% $N_2$, 10% $H_2$, 5% $CO_2$). *S. gordonii* DL1 was grown in Trypticase peptone broth (TPB) supplemented with 0.5% glucose at 37° C. under aerobic conditions.

Peptide synthesis and activity. P4 and a control peptide (peptide26 with 11 amino acids located immediately down stream of P4) were synthesized by Biomatik (Wilmington, Del.) and purified with high performance liquid chromatography (HPLC) to achieve 95% purity. The purified peptide was resuspended in nuclease/proteinase-free PBS, aliquoted, and stored at −20° C.

Monotypic biofilm assay. Attachment of P. gingivalis to saliva-coated surfaces was evaluated as described previously (O'Toole, G. A. & Kolter, R. Initiation of biofilm formation in Pseudomonas fluorescens WCS365 proceeds via multiple, convergent signalling pathways: a genetic analysis. Molecular microbiology 28, 449-461 (1998)). Briefly, P. gingivalis strains were grown to mid-log phase ($OD_{600}$=0.8) and collected by centrifugation. Bacterial cells ($10^8$) were resuspended in TSB, transferred to the wells of a 96-well polystyrene plate (Corning Inc., Corning, N.Y.) that had been precoated with human whole saliva that was diluted 2 times with PBS, and incubated at 37° C. After washing, the biofilms were stained with 1% crystal violet and destained with 95% ethanol. The absorbance of the ethanol de-staining solution at 540 nm was then determined with a spectrophotometer (Ultrospec 2100 Pro; Amersham Pharmacia Biotech).

Heterotypic biofilm assay. Heterotypic biofilms of P. gingivalis and S. gordonii were generated on a polystyrene six-well plate. S. gordonii DL1 cells ($2\times10^9$) were first incubated aerobically in saliva-coated wells at 37° C. for 3 h, and the unbound cells were removed by washing with PBS three times. P. gingivalis cells ($2\times10^9$) grown in TSB with or without P4 were collected, re-suspended in ¼ TSB (1:3 TSB and PBS), added to the wells containing streptococcal biofilms, and incubated anaerobically at 37° C. for 4 h. The number of sessile P. gingivalis in S. gordonii biofilms was determined using qPCR. The bacterial cells were lysed with lysis solution (solution A; Invitrogen, Waltham, Mass.), and DNA was extracted using an Easy-DNA kit (Invitrogen). P. gingivalis cells in the biofilms were enumerated by using a QuantiTect SYBR green PCR kit with 16S rRNA gene primers of P. gingivalis (Wu, J. & Xie, H. Role of arginine deiminase of Streptococcus cristatus in Porphyromonas gingivalis colonization. Antimicrobial agents and chemotherapy 54, 4694-4698, doi:10.1128/AAC.00284-10 (2010)). Standards used to determine numbers of P. gingivalis in the heterotypic biofilms were prepared using genomic DNA from P. gingivalis 33277. A fresh culture of 33277 was serially diluted in PBS and plated on TSB plates to obtain the colony forming units (CFUs) per milliliter for each dilution.

To determine if P4 promotes the release of P. gingivalis cells from the heterotypic biofilms and/or inhibits their re-entry, a modified biofilm assay was conducted. P. gingivalis grown without P4 was first added to wells of six-well polystyrene plates containing S. gordonii DL1 and incubated for 4 h. After removing the unbound P. gingivalis, fresh ½ TSB (1:1 TSB and PBS) containing P4 and gentamicin (50 µg/ml) was then added and the plates were incubated with gentle shaking under anaerobic conditions. Planktonic P. gingivalis were collected at three 24 h intervals, while the sessile bacterial cells were collected at the 72-h time point. Bacterial DNA was purified using an Easy-DNA kit (Invitrogen), and the P. gingivalis cells were quantitated using qPCR.

Arg- and Lys-specific proteinase activities. Gingipain activities of P. gingivalis whole cells were measured in 96-well plates as described previously (Ho M H, Chen C H, Goodwin J S, Wang B Y, Xie H. 2015. Functional Advantages of Porphyromonas gingivalis Vesicles. PLoS One 10: e0123448; Dashper, S. G. et al. Lactoferrin inhibits Porphyromonas gingivalis proteinases and has sustained biofilm inhibitory activity. Antimicrobial agents and chemotherapy 56, 1548-1556, doi:10.1128/AAC.05100-11 (2012)). P. gingivalis 33277 or W83 were anaerobically grown in 2 ml TSB with or without P4 to stationary phase ($OD_{600}$=1.2). Bacterial cells and growth media were separated by centrifugation, and the cells were re-suspended in 2 ml ice-cold TC150 buffer (pH 8.0, 5 mM cysteine, 50 mM Tris-HCl, 150 mM NaCl, and 5 mM CaCl2). The P. gingivalis cell suspension ($2.5\times10^6$ cells in 2.5 µl) or 100 µl of P. gingivalis growth media were resuspended in TC150 buffer and mixed with 100 µl substrate solution (2 mM N-a-benzoyl-Arg-p-nitroanilide (BApNA) or N-(p-tosyl)-Gly-Pro-Lys 4-nitroanilide ace-tate salt (GPK-NA), 30% isopropanol (vol/vol), 400 mM Tris-HCl (pH 8), 100 mM NaCl, and 2 mM cysteine) (Sigma-Aldrich, St. Louis, Mo.). The reaction solutions were incubated at 37° C. for 4 h, and the absorbance at 405 nm was measured by a microplate reader (Bio-Rad, Hercules, Calif.).

Bacterial invasion assay. The invasive ability of P. gingivalis was determined using an antibiotic protection assay (Xie, H., Cai, S. & Lamont, R. J. Environmental regulation of fimbrial gene expression in Porphyromonas gingivalis. Infect Immun 65, 2265-2271 (1997)). Human oral keratinocytes (HOKs, $5\times10^5$) (ScienCell Research Laboratories, Carlsbad, Calif.) were seeded in a six-well plate. After reaction with P. gingivalis 33277 or W83 for 1 h, the HOKs were washed with PBS to remove unbound bacteria and then continually cultured for another 4 h in the presence of antibiotics gentamicin (300 µg/ml) and metronidazole (200 µg/ml) to eliminate extracellular bacteria. The HOKs were then washed three times with PBS and lysed with sterile distilled $dH_2O$. The internalized bacteria were plated on TSB blood agar plates. The plates were incubated anaerobically at 37° C. for 7 days, and CFUs of P. gingivalis were enumerated.

Enzyme-linked immunosorbent assay (ELISA). ELISA was performed using a human IL-8 single analyte ELISArray kit (Qiagen, Redwood City, Calif.), according to the manufacturer's instructions. HOKs ($1\times10^5$) were exposed to P. gingivalis ($1\times10^6$) grown with or without P4 for 2 and 18 h. The culture media of HOKs were collected and analyzed by ELISA. L-8 was quantitated using a standard curve of the cytokine.

Statistical analyses. A Student's t-test was used to determine the statistical significance of differences in functions and growth rates of P. gingivalis strains grown in the presence or absence of P4. A $p<0.05$ was considered significant. All assays were performed with three biological replicates.

Results

Figure 9A:
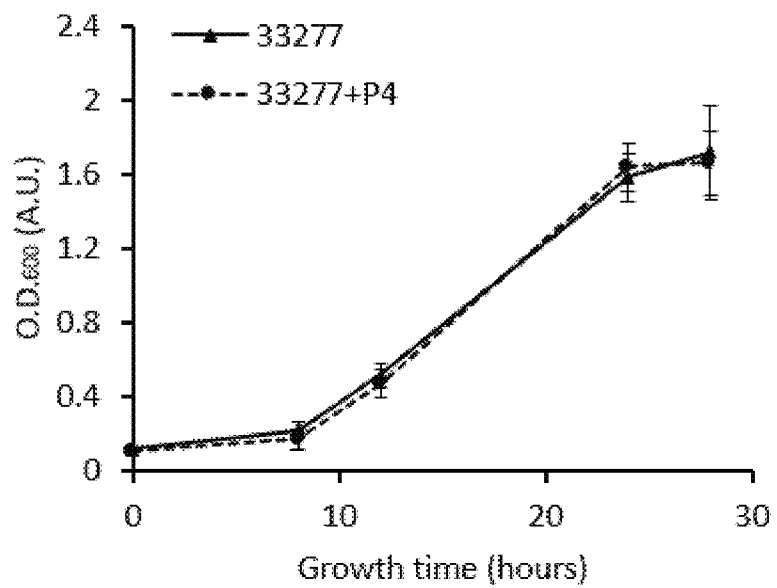
FIGS. 9A-9B show a comparison of the growth curves of *P. gingivalis* strains grown in the presence or absence of P4.
Figure 9B:
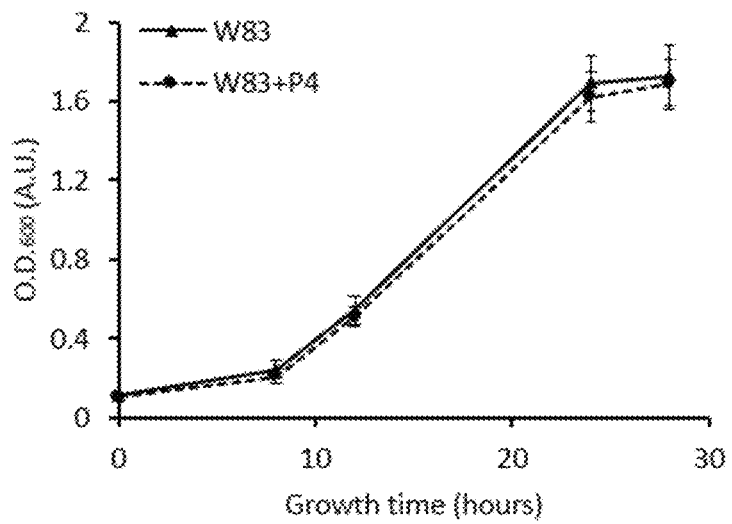

Effect of P4 on biofilm formation of P. gingivalis. P. gingivalis strains 33277 and W83 from ATCC were selected as representatives of fimbriated, non-encapsulated and non-fimbriated, encapsulated lineages, respectively, to examine alteration of phenotypic properties of P. gingivalis in response to P4. As shown in FIGS. 9A and 9B, growth rates of P. gingivalis 33277 or W83 were not significantly changed in the presence of P4 (24 µM) compared to growth without P4. This observation suggests a killing-independent mechanism of P4 action, which is in an agreement with our earlier finding that P4 repress expression and production of fimbrial proteins and gingipains in P. gingivalis. While the predominant niche of P. gingivalis is the subgingival area, the organism also colonizes supragingival plaque and oral mucosal surfaces. Indeed these sites, which are exposed to the salivary fluid phase, may represent early colonization events. Hence, P. gingivalis strains grown with or without P4 were then tested for their ability to attach to saliva-covered surfaces. After a 24 h incubation, an approximately 25% decrease of attachment was detected with P. gingivalis 33277 grown with P4 (24 µM) compared to the control without P4 (FIG. 10A), while after 48 h the decrease in attachment reached 70%. A control peptide (peptide26 with 11 amino acids located immediately down stream of P4) was also tested for its role in biofilm formation of P. gingivalis, and it did not significantly affect the biofilm formation. The effect om monotypic biofilm formation by W83 was also tested with the bacterial cells grown with 24 or 48 µM P4. The ability of W83 to form biofilms was lower than that of 33277, and an impact of P4 on biofilm formation by W83 was not observed after 24 h. However, after 48 h a 33% and 54% reduction in biofilm formation was observed for bacteria grown with 24 or 48 µM P4 (FIG. 10B). These results indicate that P4 can suppress biofilm formation by both 33277 and W83, with more efficient inhibition occurring with 33277 likely due to the involvement of fimbrial adhesins in biofilm formation by 33277.

P. gingivalis and S. gordonii dual-species communities are one of the best documented examples of synergistic oral bacterial interactions. The surface molecules involved in co-adhesion are well characterized, and include FimA and Mfa1 of P. gingivalis and streptococcal GAPDH and SspA/B. We postulated that P4 could prevent the formation of heterotypic P. gingivalis-S. gordonii biofilms by repressing the expression of fimA and mfa1. To test this, S. gordonii DL1 substrata were first established on saliva-coated wells, and reacted with P. gingivalis grown with or without P4 (24 µM). The amount of P. gingivalis 33277 bound to the S. gordonii DL1 biofilms was determined with qPCR. The number of P. gingivalis grown without P4 was 2.5-fold higher than that of the bacteria grown with P4 (FIG. 11). Not surprisingly, binding of P. gingivalis W83, an afrimbriated strain, to S. gordonii DL1 biofilms was not observed (data not shown), which further confirms the role of FimA and Mfa1 fimbriae in the interaction of P. gingivalis and S. gordonii.

Figure 12A:
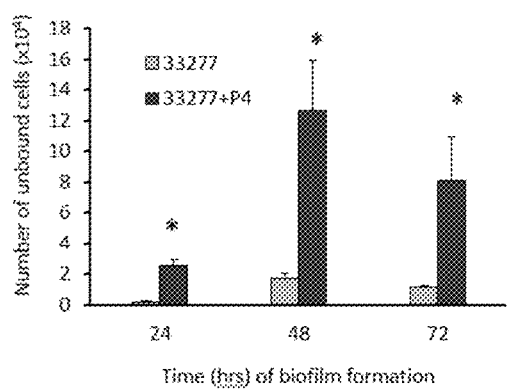
Figure 12B:
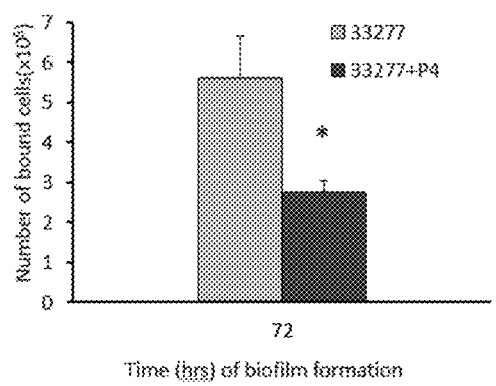
Figure 12C:
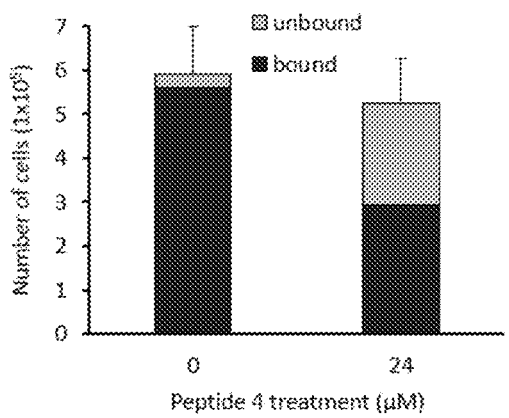
Figure 12D:
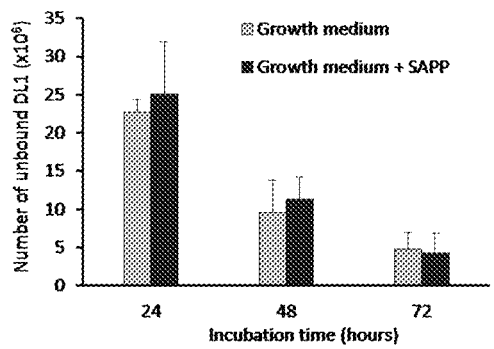

Tests were then performed to determine if P4 can reduce the numbers of P. gingivalis cells in established heterotypic biofilms. To do this, heterotypic biofilms of S. gordonii-P. gingivalis that were grown without P4 were generated. After the removal of unbound bacteria, P4 (24 µM) was added. Planktonic P. gingivalis was collected three times in a 24 h interval, and the biofilm was collected after 72 h. The numbers of planktonic or sessile P. gingivalis were determined using qPCR. Levels of planktonic P. gingivalis cells were significantly increased following P4 treatment (FIG. 12A). Consistent with this, the number of P. gingivalis in the heterotypic biofilms was negatively correlated with that in the planktonic phase, and introduction of P4 to P. gingivalis-S. gordonii heterotypic biofilms reduced the number of P. gingivalis by approximately 50% after 72 h (FIG. 12B). There was no significant difference in the total P. gingivalis cell number with or without P4 (FIG. 12C), and numbers of S. gordonii in the growth media did not alter in the presence or absence of P4 (FIG. 12D). These data suggest that P4 does not effect bacterial viability; rather, it promotes detachment of P. gingivalis cells in the heterotypic biofilms and inhibits their reentry the biofilm. Furthermore, P4 does not impact colonization of the health-related microbiota in this model system.

Impact of P4 on intracellular invasion of P. gingivalis. The adherence of P. gingivalis to epithelial cells is mediated primarily by FimA and adhesive domains of gingipains. Adherence subsequently initiates bacterial internalization of host cells. Since P4 represses FimA and gingipain production, it was postulated that it may also inhibit P. gingivalis invasion of human oral keratinocytes (HOKs). Antibiotic protection assays were conducted to compare the invasive ability of P. gingivalis 33277 and W83 grown with or without P4. Consistent with previous reports, P. gingivalis W83 was much less efficient than strain 33277 in invading HOKs (FIGS. 13A and 13B).

Moreover, the invasion efficiency of 33277 grown with P4 (24 µM) was reduced by approximate 4.8 fold compared to the control without P4, while a 5.2-fold difference in invasion efficiency was observed with W83 grown in the presence or absence of P4 (48 µM).

Figure 6B:
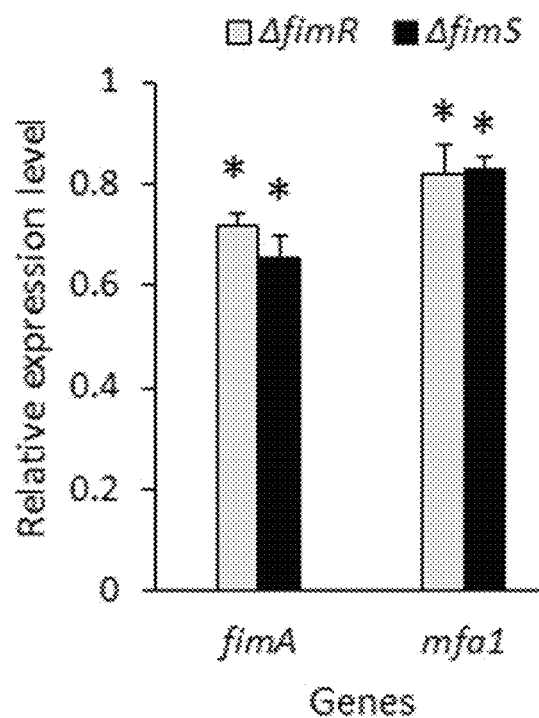
Figure 14A:
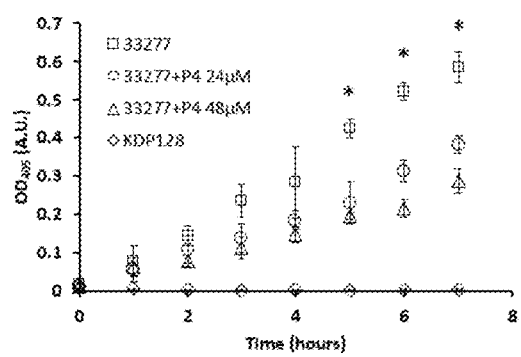
Figure 14B:
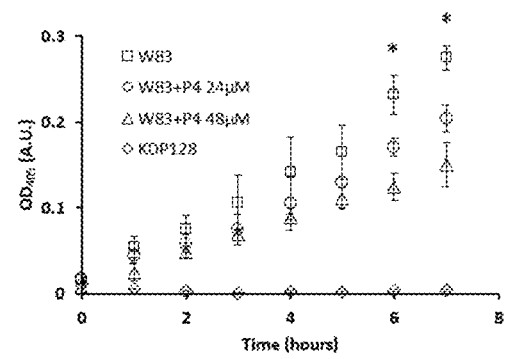
Figure 14C:
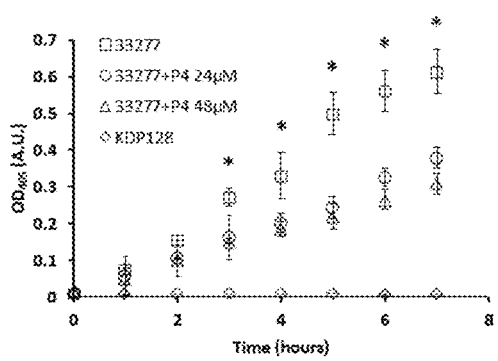
Figure 14D:
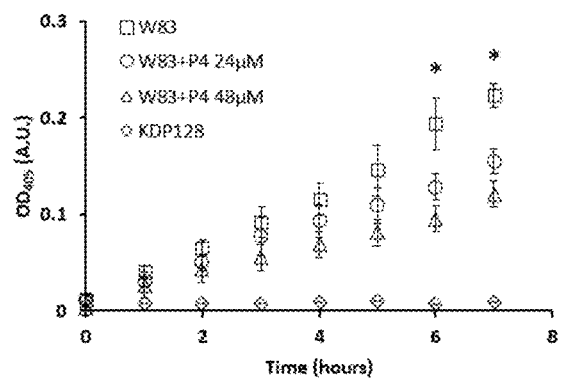

Effect of P4 on gingipain enzymatic activity. P. gingivalis gingipains are multi-functional proteins with adhesive and catalytic domains. Arginine-specific or lysine-specific activities in P. gingivalis strains grown with or without P4 were tested and compared. An rgpA, rgpB, and kgp triple mutant (KDP128) was used as a negative control, and as expected, no arginine- or lysine-specific enzyme activities were detected in the mutant (FIGS. 14A-14D). Cell-associated arginine-specific protease activity of P. gingivalis 33277 grown with P4 (48 µM) was decreased by 50%, while a 46% reduction was found in W83 under the same experimental conditions, compared with the control without P4 (FIG. 14A). P4 inhibited cell-associated lysine-specific protease activity of P. gingivalis 33277 and W83 to a similar degree (FIG. 14B 6b). Rgp and Kgp activities in the growth media of 33277 and W83 were also monitored to determine the levels of secreted gingipains. After exposure to P4 (48 µM), P. gingivalis 33277 exhibited a greater than 2.5-fold decrease in Rgp activity, and 2-fold less in Kgp activity (FIGS. 14C and 14D). Rgp and Kgp activity in culture supernatants was also 50% lower after W83 was exposed to P4 (48 µM). Significantly lower protease activities of Rgp and Kgp induced by P4 can be predicted to reduce the virulence potential of P. gingivalis.

Modulation of IL-8 levels by P4. P. gingivalis is known to selectively impair the production of certain cytokines and chemokines, such as IL-8. Thus, we compared the accumulation of IL-8 in the growth media of HOKs exposed to P. gingivalis grown with or without P4 (48 µM) using an ELISA. The results showed that the ability of P. gingivalis 33277 or W83 to reduce the accumulation of 11-8 was significantly diminished by P4 (FIG. 15). These data indicate that P4 has the potential to modulate manipulation of the innate immune response by P. gingivalis.

Discussion

Treatment of chronic and other forms of periodontitis usually involves physical removal of the plaque biofilm sometimes supplemented by systemic or local administration of antibiotics, especially in the cases of severe and refractory manifestations of the disease. While the adjunctive use of antibiotics may improve the results of the mechanical therapy, meta-analyses suggest that the benefits of antibiotic treatment must be balanced against their side effects. Concerns regarding the use of antibiotics include breaking the symbiotic or mutualistic relationships between host and commensal microbiota, and emerging oral bacterial resistance to antibiotics. Therefore, targeting specific pathogenic bacteria, rather than non-selectively inhibiting both pathogens and commensal bacteria, has emerged as a strategic goal for maintaining a healthy oral microbiota.

Fimbrial proteins, FimA and Mfa1, and gingipains, RgpA, RgpB, and Kgp, are well-established virulence factors of P. gingivalis. Genes for mfa1 and fimA are present in the genomes of 20 of 21 *P. gingivalis* strains isolated worldwide over a 25 year time period, and thus far, all tested *P. gingivalis* strains produce gingipains that are both membrane associated and secreted in soluble form. The primary role of FimA and Mfa1 is to promote the bacterial attachment to various oral surfaces, which leads to biofilm formation and internalization of epithelial cells. The gingipains include two arginine and one lysine specific cysteine proteinases (RgpA, RgpB, and Kgp). Gingipains are multifunctional proteins that have important roles in nutrient acquisition and protein processing, and can also degrade host matrix proteins and immune effector molecules. Gingipains play an important role in biofilm formation through the C-terminal adhesive regions of RgpA and Kgp, or through processing profimbrillin. Animal studies with a murine lesion model ang using gingipain mutants, found that gingipains, Kgp in particular, are primary contributors to the formation of skin abscesses. Moreover, using the same animal model, pretreatment of *P. gingivalis* with a Kgp inhibitor also decreased bacterial virulence, which demonstrates an essential role of gingipains in *P. gingivalis* infection. A previous study by Wilensky et al. also showed that alveolar bone loss was only observed in mice orally infected with RgpA-expressing *P. gingivalis* strains. Therefore, inhibition of these *P. gingivalis* virulence factors has become the focus of therapeutic strategies for prevention and treatment of periodontitis, and a long list of gingipain inhibitors has been discovered, including synthetic compounds, proteins and peptides, and extracts from plants. Nonetheless, the therapeutic potential of disruption of other pathogenic processes of *P. gingivalis* is also under investigation. Several molecules derived from marine natural products were identified as inhibitors of *P. gingivalis-S. gordonii* heterotypic community formation through repression of expression of mfa1 and fimA. Other promising biofilm inhibitors are small peptides representing the binding domain (BAR) of *S. gordonii* SspB, which has been shown to disrupt *P. gingivalis-S. gordonii* communities and prevent bone loss in a mouse model. One limitation of these inhibitors is that each of them only targets a single virulence factor of *P. gingivalis*, either a fimbrial protein or gingipains. In this report, we show that P4 derived from *S. cristatus* ArcA has a much broader spectrum and is able to impede several virulence factors simultaneously. Such multiplicity of action greatly increases the value of this peptide as a potent inhibitor capable of eliminating *P. gingivalis* strains expressing virulence factors differentially.

In this study, it has been demonstrated that P4 does not impact growth of *P. gingivalis* but significantly reduces the numbers of *P. gingivalis* cells in both monotypic biofilms and *P. gingivalis-S. gordonii* heterotypic biofilms. A reduction of *P. gingivalis* cell number can be predicted to lead to a loss of competitive edge and a disruption of polymicrobial synergy. Another significant finding is that P4 not only inhibits *P. gingivalis* biofilm formation but also disrupts established biofilms. Although the mechanism is unclear, it is speculated that P4 disrupts attachment and inhibits re-entry of the detached bacteria to the biofilm. The dispersed *P. gingivalis* cells may be eliminated from the oral cavity due to reduced ability to attach to oral surfaces and to invade host cells. Directly targeting *P. gingivalis* attachment by P4 should therefore stabilize a healthy microbiota and maintain homeostasis between the oral microbiota and host immune systems hence, it may be sufficient to prevent and treat *P. gingivalis* associated-periodontitis.

It has been reported that the expression of IL1α, IL-β, IL6, IL-8, IL-10, and NF-κB is modulated in oral epithelial cells infected with *P. gingivalis*. In contrast to many periodontal colonizers that induce expression of IL-8 in gingival epithelial cells, *P. gingivalis* can inhibit IL-8 production, suggesting a unique role for *P. gingivalis* in regulating epithelial cell chemokine responses. The ability of *P. gingivalis* to modulate IL-8 levels could play a pivotal role in initiating periodontitis, since this chemokine is involved in sustaining a healthy periodontium by maintaining a gradient for neutrophil recruitment into the gingival crevice. The P4 peptide attenuate the ability of *P. gingivalis* to reduce the accumulation of IL-8 in epithelial cell culture supernatants, suggesting that P4 is able to partially restore the impairment of host immunity by *P. gingivalis*, which may facilitate maintenance of periodontal tissue homeostasis.

In conclusion, the inhibitory role of P4 in biofilm formation, invasion, and gingipain activity of *P. gingivalis* has been assessed. It was demonstrated that a unique aspect of this peptide is that it efficiently reduced all these virulence-associated properties of *P. gingivalis*. The ability of P4 to selectively disperse *P. gingivalis* from dental plaque and attenuate its virulence potential makes it as an attractive agent for controlling the composition of microbial communities and maintaining a healthy microbiota.

Working Example 4

Cytotoxicity and Stability of P4

To examine the cytotoxic effects of P4, plasma membrane damage of HOKs was determined by the Pierce LDH Cytotoxicity Assay Kit. HOKs were seeded into a 6-well plate at a density of $1 \times 10^5$/well and cultured in Oral Keratinocyte Medium supplemented with antibiotics (100 U/mL penicillin and 100 µg/mL streptomycin) and 10% fetal calf serum at 37° C. in a humidified chamber with 5% $CO_2$ for 24 h. The cells were then incubated with the growth medium supplemented with P4 (50 or 200 µM) for 48 h. The growth medium was collected for an LDH cytotoxicity assay according to the manufacturer's instructions (Thermo Scientific). To measure the effect of P4 on HOK apoptosis, HOKs were harvested and stained with Annexin V-FITC Apoptosis Kit (Invitrogen), which is able to stain both apoptotic cells and dead cells. Flow cytometric analysis was performed to quantitate apoptotic cells and dead cells (annexin V+/PI+). As shown in FIGS. 9A and 9B, P4 at concentrations as high as 200 µM (approximately 200-fold greater than that required to repress expression of fimA and rpg by 50%, ID50) did not induce cell membrane damage and apoptosis of HOKs To determine P4 stability in solution, P4 was incubated in $H_2O$, PBS, and whole saliva at 37° C. for 24 h. P4 in each sample was compared using LC-MS/MS analysis. Briefly, 2 µM P4 was injected on C18 nano-clumn and run with 5-20% of 0.1% FA in acetonitrile for 30 min. MS spectra were acquired in a positive mode on Orbitrap LTQ XL (Thermo). As shown in TABLE 4, P4 stability was not affected in $H_2O$ and PBS after 24 h incubation, but a gradual reduction of the signal was detected after P4 was incubated in the diluted whole saliva (PBS:saliva, 1:1) after 0, 0.5, 1, 2, 4, and 24 h, and the signal was completely diP4eared to the background noise after 48 h. It should be noted that these results show only relative levels of P4 in these solutions, and we cannot conclude that only one tenth of P4 is undegraded. However, the signal was observed after a 24 h incubation, suggesting that P4 can maintain in saliva for at least 24 h at certain level.

TABLE 4

| P4 treated with | Treating time (hour) | Signal Intensity of 331.45 m/z peak |
|---|---|---|
| H$_2$O | 0 | 4.8 × 10$^6$ ± 4.5 × 10$^5$ |
| H$_2$O | 24 | 2.1 × 10$^6$ ± 1.3 × 10$^5$ |
| PBS | 24 | 4.6 × 10$^6$ ± 4.2 × 10$^5$ |
| Saliva | 0 | 3.9 × 10$^6$ ± 3.1 × 10$^5$ |
| Saliva | 0.5 | 3.6 × 10$^6$ ± 4.0 × 10$^5$ |
| Saliva | 1 | 2.4 × 10$^6$ ± 2.2 × 10$^5$ |
| Saliva | 2 | 1.7 × 10$^6$ ± 4.2 × 10$^5$ |
| Saliva | 4 | 8.8 × 10$^5$ ± 2.7 × 10$^4$ |
| Saliva | 24 | 4.2 × 10$^5$ ± 3.9 × 10$^4$ |
| Saliva | 48 | 6.0 × 10$^3$ ± 4.1 × 10$^2$ |

I. EMBODIMENTS

In addition to anything described above or currently claimed, it is specifically contemplated that any of the following embodiments may be claimed. Emb. 1: An isolated peptide that binds to a *P. gingivalis* surface protein, the peptide having a sequence of at least 60% identity with at least one of: SEQ ID NOS: 2-7. Emb. 2: A pharmaceutical composition for treating or preventing a plaque-related condition or symptom, the composition comprising a compound, the compound comprising the peptide of emb. 1. Emb. 3: A use of a compound in the manufacture of a pharmaceutical composition for treating or preventing a plaque-related condition or symptom, wherein the compound comprises the peptide of emb. 1. Emb. 4: Any one of embs. 2-3, wherein the pharmaceutical composition is formulated for local administration. Emb. 5: Any one of embs. 2-4, wherein the pharmaceutical composition is at least one of a dentifrice, buccal preparation, sublingual preparation, an oral ointment, an oral cream, an oral paste, an oral emulsion, and a chewing gum. Emb. 6: Any one of embs. 2-5, wherein the peptide is present in a therapeutically effect amount to treat or prevent the plaque-related condition or symptom in a subject in need thereof. Emb. 7: Any one of embs. 2-6, wherein the pharmaceutical composition is a dentifrice. Emb. 8: Any one of embs. 2-7, wherein the pharmaceutical composition comprises a preservative. Emb. 9: Any one of embs. 2-8, wherein the pharmaceutical composition comprises a pharmaceutically acceptable carrier. Emb. 10: Any one of embs. 2-9, wherein the pharmaceutical composition comprises a pharmaceutically acceptable carrier selected from the group consisting of: vehicles, adjuvants, surfactants, suspending agents, emulsifying agents, inert fillers, diluents, excipients, wetting agents, binders, lubricants, buffering agents, disintegrating agents and carriers, accessory agents, coloring agents, and flavoring agents. Emb. 11: A method of treating or preventing a plaque-related condition or symptom in a subject, the method comprising locally administering to the dental and/or gingival surfaces of the subject a therapeutically effective amount of a compound comprising the peptide of emb. 1. Emb. 12: The method of emb. 11, wherein the subject is in need of treatment or preventative treatment of the plaque-related condition or symptom. Emb. 13: Any one of embs. 2-12, wherein the plaque-related condition or symptom is selected from the group consisting of: dental caries, gingivitis, tartar, periodontitis, atherosclerosis, human immunodeficiency virus (HIV) disease, tooth loss, coronary artery disease, stroke, premature birth, low birth weight, poorly controlled diabetes, respiratory problems, rheumatoid arthritis, and asthma. Emb. 14: A method of reducing the likelihood of the formation of a biofilm containing a population of *Porphyromonas gingivalis* on a surface, the method comprising exposing the surface to an effective concentration of a compound comprising the peptide of emb. 1. Emb. 15: A method of reducing the expression of a bacterial virulence gene or biofilm-associated gene in a bacterium, the method comprising exposing the bacterium to an effective concentration of a compound comprising a peptide having a sequence of at least 60% identity with at least one of: SEQ ID NOS: 3-7; wherein the bacterial gene is selected from the group consisting of: a fimbrillin gene, fimA, a gingipain gene, mfa1, rgpA/B, rgpA, and kgp. Emb. 16: The method of emb. 15, wherein the bacterial gene is fimA. Emb. 17: The method of emb. 15, wherein the bacterium is *Porphyromonas gingivalis*. Emb. 18: Any one of embs. 15-17, wherein the method is performed in vitro. Emb. 19: Any one of embs. 15-18, wherein the exposing comprises contacting. Emb. 20: Any one of embs. 15-19, wherein the exposing comprises exposing the bacterium in a subject in need thereof. Emb. 21: A nucleic acid encoding the peptide of emb. 1. Emb. 22: A nucleic acid that is complementary to the nucleic acid of emb. 23. Emb. 23: A cell comprising the nucleic acid of any of embs. 22-24. Emb. 24: A vector comprising the nucleic acid of any of embs. 22-25. Emb. 25: Any one of embs. 1-26, wherein the peptide has at least 60% identity with at least one of: IRGRETKK (SEQ ID NO: 3), NHMFADTRNRE (SEQ ID NO: 4), VYNREEDTRIEGGDEL (SEQ ID NO: 5), NIFKKNVGFKK (SEQ ID NO: 6), and ELVRGRGGPRCMSMPF (SEQ ID NO: 7). Emb. 26: Any one of embs. 1-25, wherein the peptide has no significant arginine deiminase activity. Emb. 27: Any one of embs. 1-26, wherein the peptide is a fragment of positions 208-409 of SEQ ID NO: 1. Emb. 28: Any one of embs. 1-27, wherein the peptide is no more than 202 amino acids in length. Emb. 29: Any one of embs. 1-28, wherein the peptide comprises only exemplary conservative substitutions as shown in TABLE 1 compared to said at least one of: SEQ ID NOS: 2-7. Emb. 30: Any one of embs. 1-29, wherein the peptide comprises only preferred conservative substitutions as shown in TABLE 1 compared to said at least one of: SEQ ID NOS: 2-7. Emb. 31: Any one of embs. 1-30, wherein the peptide has a sequence of at least 70, 75, 80, 85, 90, 95, 99, or 100% identity with at least one of: SEQ ID NOS: 2-7. Emb. 32: Any one of embs. 1-31, wherein the peptide has a sequence of at least 90, 95, 99, or 100% identity with at least one of: SEQ ID NOS: 2-7. Emb. 33: Any one of embs. 1-32, wherein the peptide has at least 60% identity with SEQ ID NO: 6, and wherein the compound comprises not more than 4-8 amino acid residues flanking said peptide on at least one of the N-terminal or C-terminal ends. Emb. 34: Any one of embs. 2-33, wherein the compound consists of the peptide. Emb. 35: Any one of embs. 1-34, wherein the length of the peptide is no more than 200, 190, 180, 170, 160, 150, 140, 130, 120, 110, 100, 90, 80, 70, 60, 50, 40, 30, 20, 16, 15, 14, 13, 12, 11, 10, 9, 8, 7, 6, or 5 amino acid residues long. Emb. 36: Any one of embs. 1-35, wherein the peptide has only conservative substitutions compared to said at least one of: SEQ ID NOS: 2-7. Emb. 37: Any one of embs. 1-36, wherein the peptide has only exemplary substitutions shown in TABLE 1 compared to said at least one of: SEQ ID NOS: 2-7. Emb. 38: Any one of embs. 1-37, wherein the peptide has only preferred substitutions shown in TABLE 1 compared to said at least one of: SEQ ID NOS: 2-7. Emb. 39: Any one of embs. 1-38, wherein the peptide consists of a peptide having a sequence of NIFKKNVGFKK.

J. CONCLUSIONS

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

The following is claimed:

1. A method of treating a biofilm comprising *Porphyromonas gingivalis*, the method comprising administering to a subject a therapeutically effective amount of a compound comprising a peptide consisting of the sequence of SEQ ID NO: 6, wherein the peptide has no arginine deiminase activity.

2. The method of claim 1, wherein the peptide has been purified.

3. The method of claim 1, wherein the compound is formulated for topical administration to the subject.

4. The method of claim 1, wherein administering to the subject comprises exposing the dental and/or gingival surfaces of the subject to the compound.

5. The method of claim 1, wherein the compound is formulated for systemic administration to the subject.

6. The method of claim 1, wherein the compound is at least one of a dentifrice, buccal preparation, sublingual preparation, an oral ointment, an oral cream, an oral paste, an oral emulsion, and a chewing gum.

7. The method of claim 1, wherein the compound comprises a pharmaceutically acceptable carrier selected from the group consisting of: vehicles, adjuvants, surfactants, suspending agents, emulsifying agents, inert fillers, diluents, excipients, wetting agents, binders, lubricants, buffering agents, disintegrating agents and carriers, accessory agents, coloring agents, and flavoring agents.

8. The method of claim 1, wherein the compound is formulated for local administration to the subject.

9. The method of claim 1, wherein the compound further comprises a preservative.

10. A method of treating a biofilm comprising *Porphyromonas gingivalis* in a subject, the method comprising administering to the mouth of the subject a compound comprising a peptide consisting of the sequence of SEQ ID NO: 6, wherein the peptide has no arginine deiminase activity.

11. The method of claim 10, wherein the peptide has been purified.

12. The method of claim 10, wherein the the compound is formulated for sustained release of the peptide.

13. The method of claim 10, wherein the compound is formulated for transdermal administration to the mouth of the subject.

14. The method of claim 10, wherein the compound is formulated for topical administration to the mouth of the subject.

15. The method of claim 10, wherein administering to the mouth of the subject comprises administering the compound locally to the dental and/or gingival surfaces of the subject.

16. The method of claim 10, wherein the compound is at least one of a dentifrice, buccal preparation, sublingual preparation, an oral ointment, an oral cream, an oral paste, an oral emulsion, and a chewing gum.

17. The method of claim 10, wherein the compound is a dentifrice selected from the group consisting of: a paste; a gel, a mouthwash, a powder, and a tooth soap.

18. The method of claim 10, wherein the compound further comprises a preservative.

19. The method of claim 10, wherein the compound further comprises a pharmaceutically acceptable carrier.

20. The method of claim 19, wherein the pharmaceutically acceptable carrier is selected from the group consisting of: vehicles, adjuvants, surfactants, suspending agents, emulsifying agents, inert fillers, diluents, excipients, wetting agents, binders, lubricants, buffering agents, disintegrating agents and carriers, accessory agents, coloring agents, and flavoring agents.

* * * * *